United States Patent [19]
Jacobs et al.

[11] Patent Number: 5,708,157
[45] Date of Patent: Jan. 13, 1998

[54] SECRETED PROTEINS AND POLYNUCLEOTIDES ENCODING THEM

[75] Inventors: Kenneth Jacobs, Newton; John M. McCoy, Reading; Edward R. LaVallie, Tewskbury; Lisa A. Racie; David Merberg, both of Acton; Maurice Treacy, Chestnut Hill; Cheryl Evans, Brookline; Vikki Spaulding, Billerica, all of Mass.

[73] Assignee: Genetics Institute, Inc., Cambridge, Mass.

[21] Appl. No.: 686,878

[22] Filed: Jul. 26, 1996

[51] Int. Cl.⁶ .................. C12N 15/10; C12N 5/10; C12N 15/12; C07K 14/47
[52] U.S. Cl. .............. 536/23.5; 435/691; 435/320.1; 435/325; 435/252.3; 435/254.11; 530/300; 530/350; 530/850; 424/559; 514/12
[58] Field of Search .................. 435/69.1, 325, 435/252.3, 254.11, 320.1; 424/78.01, 185.1, 278.1, 559; 514/44–46; 530/300, 350, 351, 380, 850, 252, 853; 536/23.1, 26.13

[56] References Cited

U.S. PATENT DOCUMENTS

| | | | |
|---|---|---|---|
| 3,223,592 | 12/1965 | Kinichiro et al. | 195/28 |
| 3,832,471 | 8/1974 | Siregar | 426/2 |
| 3,920,853 | 11/1975 | Middendorf et al. | 426/104 |
| 4,267,195 | 5/1981 | Boudreau et al. | 426/2 |

OTHER PUBLICATIONS

Rothenfluh et al., Analusis of patterns of DNA sequence variation in flanking and coding regions of murine germ-line immunoglobulin heavy–chain variable genes:evolutionary implications, Proc. Natl. Acad. Sci. USA, 95(15): 12163–12167, Nov. 1994.

Promega Protocols and Applications Guide, Titus, ed., Promega Corp., USA, pp. 394–397, 1991.

Stratagene Cloning Systems (catalogue), pp. 124–125, 1994.

Genbank Accession No. U43394, May 1996.

Genbank Accession No. J01917, Mar. 1996.

*Primary Examiner*—Stephen Walsh
*Assistant Examiner*—Claire M. Kaufman
*Attorney, Agent, or Firm*—Scott A. Brown; Suzanne A. Sprunger; Thomas J. DesRosier

[57] ABSTRACT

Novel polynucleotides and the proteins encoded thereby are disclosed.

21 Claims, No Drawings

SECRETED PROTEINS AND POLYNUCLEOTIDES ENCODING THEM

FIELD OF THE INVENTION

The present invention provides novel polynucleotides and proteins encoded by such polynucleotides, along with therapeutic, diagnostic and research utilities for these polynucleotides and proteins.

BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

SUMMARY OF THE INVENTION

In one embodiment, the present invention provides a composition comprising an isolated polynucleotide selected from the group consisting of:

(a) a polynucleotide comprising the nucleotide sequence of SEQ ID NO:1;

(b) a polynucleotide comprising the nucleotide sequence of SEQ ID NO:1 from nucleotide 218 to nucleotide 628;

(c) a polynucleotide comprising the nucleotide sequence of the full length protein coding sequence of clone AJ26_3 deposited under accession number ATCC 98115;

(d) a polynucleotide encoding the full length protein encoded by the cDNA insert of clone AJ26_3 deposited under accession number ATCC 98115;

(e) a polynucleotide comprising the nucleotide sequence of the mature protein coding sequence of clone AJ26_3 deposited under accession number ATCC 98115;

(f) a polynucleotide encoding the mature protein encoded by the cDNA insert of clone AJ26_3 deposited under accession number ATCC 98115;

(g) a polynucleotide encoding a protein comprising the amino acid sequence of SEQ ID NO:2;

(h) a polynucleotide encoding a protein comprising a fragment of the amino acid sequence of SEQ ID NO:2 having biological activity;

(i) a polynucleotide which is an allelic variant of a polynucleotide of (a)–(d) above;

(j) a polynucleotide which encodes a species homologue of the protein of (g) or (h) above.

Preferably, such polynucleotide comprises the nucleotide sequence of SEQ ID NO:1 from nucleotide 218 to nucleotide 628; the nucleotide sequence of the full length protein coding sequence of clone AJ26_3 deposited under accession number ATCC 98115; or the nucleotide sequence of the mature protein coding sequence of clone AJ26_3 deposited under accession number ATCC 98115. In other preferred embodiments, the polynucleotide encodes the full length or mature protein encoded by the cDNA insert of clone AJ26_3 deposited under accession number ATCC 98115. In yet other preferred embodiments, the present invention provides a polynucleotide encoding a protein comprising the amino acid sequence of SEQ ID NO:2 from amino acid 27 to amino acid 82.

Other embodiments provide the gene corresponding to the cDNA sequence of SEQ ID NO:1 or SEQ ID NO:.

In other embodiments, the present invention provides a composition comprising a protein, wherein said protein comprises an amino acid sequence selected from the group consisting of:

(a) the amino acid sequence of SEQ ID NO:2;

(b) the amino acid sequence of SEQ ID NO:2 from amino acid 27 to amino acid 82;

(c) fragments of the amino acid sequence of SEQ ID NO:2; and (d) the amino acid sequence encoded by the cDNA insert of clone AJ26_3 deposited under accession number ATCC 98115; the protein being substantially free from other mammalian proteins. Preferably such protein comprises the amino acid sequence of SEQ ID NO:2 or the amino acid sequence of SEQ ID NO:2 from amino acid 27 to amino acid 82.

In one embodiment, the present invention provides a composition comprising an isolated polynucleotide selected from the group consisting of:

(a) a polynucleotide comprising the nucleotide sequence of SEQ ID NO:5;

(b) a polynucleotide comprising the nucleotide sequence of SEQ ID NO:5 from nucleotide 1 to nucleotide 591;

(c) a polynucleotide comprising the nucleotide sequence of the full length protein coding sequence of clone BL89_10 deposited under accession number ATCC 98115;

(d) a polynucleotide encoding the full length protein encoded by the cDNA insert of clone BL89_10 deposited under accession number ATCC 98115;

(e) a polynucleotide comprising the nucleotide sequence of the mature protein coding sequence of clone BL89_10 deposited under accession number ATCC 98115;

(f) a polynucleotide encoding the mature protein encoded by the cDNA insert of clone BL89_10 deposited under accession number ATCC 98115;

(g) a polynucleotide encoding a protein comprising the amino acid sequence of SEQ ID NO:6;

(h) a polynucleotide encoding a protein comprising a fragment of the amino acid sequence of SEQ ID NO:6 having biological activity;

(i) a polynucleotide which is an allelic variant of a polynucleotide of (a)–(d) above;

(j) a polynucleotide which encodes a species homologue of the protein of (g) or (h) above.

Preferably, such polynucleotide comprises the nucleotide sequence of SEQ ID NO:5 from nucleotide 1 to nucleotide 591; the nucleotide sequence of the full length protein coding sequence of clone BL89_10 deposited under accession number ATCC 98115; or the nucleotide sequence of the mature protein coding sequence of clone BL89_10 deposited under accession number ATCC 98115. In other preferred embodiments, the polynucleotide encodes the full length or mature protein encoded by the cDNA insert of clone BL89_10 deposited under accession number ATCC 98115. In yet other preferred embodiments, the present invention provides a polynucleotide encoding a protein comprising the amino acid sequence of SEQ ID NO:6 from amino acid 80 to amino acid 105.

Other embodiments provide the gene corresponding to the cDNA sequence of SEQ ID NO:5, SEQ ID NO:4 or SEQ ID NO:7.

In other embodiments, the present invention provides a composition comprising a protein, wherein said protein comprises an amino acid sequence selected from the group consisting of:

(a) the amino acid sequence of SEQ ID NO:6;
(b) the amino acid sequence of SEQ ID NO:6 from amino acid 80 to amino acid 105;
(c) fragments of the amino acid sequence of SEQ ID NO:6; and
(d) the amino acid sequence encoded by the cDNA insert of clone BL89_10 deposited under accession number ATCC 98115; the protein being substantially free from other mammalian proteins. Preferably such protein comprises the amino acid sequence of SEQ ID NO:6 or the amino acid sequence of SEQ ID NO:6 from amino acid 80 to amino acid 105.

In one embodiment, the present invention provides a composition comprising an isolated polynucleotide selected from the group consisting of:

(a) a polynucleotide comprising the nucleotide sequence of SEQ ID NO:8;
(b) a polynucleotide comprising the nucleotide sequence of SEQ ID NO:8 from nucleotide 1 to nucleotide 390;
(c) a polynucleotide comprising the nucleotide sequence of the full length protein coding sequence of clone BV239_2 deposited under accession number ATCC 98115;
(d) a polynucleotide encoding the full length protein encoded by the cDNA insert of clone BV239_2 deposited under accession number ATCC 98115;
(e) a polynucleotide comprising the nucleotide sequence of the mature protein coding sequence of clone BV239_2 deposited under accession number ATCC 98115;
(f) a polynucleotide encoding the mature protein encoded by the cDNA insert of clone BV239_2 deposited under accession number ATCC 98115;
(g) a polynucleotide encoding a protein comprising the amino acid sequence of SEQ ID NO:9;
(h) a polynucleotide encoding a protein comprising a fragment of the amino acid sequence of SEQ ID NO:9 having biological activity;
(i) a polynucleotide which is an allelic variant of a polynucleotide of (a)–(d) above;
(j) a polynucleotide which encodes a species homologue of the protein of (g) or (h) above.

Preferably, such polynucleotide comprises the nucleotide sequence of SEQ ID NO:8 from nucleotide 1 to nucleotide 390; the nucleotide sequence of the full length protein coding sequence of clone BV239_2 deposited under accession number ATCC 98115; or the nucleotide sequence of the mature protein coding sequence of clone BV239_2 deposited under accession number ATCC 98115. In other preferred embodiments, the polynucleotide encodes the full length or mature protein encoded by the cDNA insert of clone BV239_2 deposited under accession number ATCC 98115. In yet other preferred embodiments, the present invention provides a polynucleotide encoding a protein comprising the amino acid sequence of SEQ ID NO:9 from amino acid 50 to amino acid 130.

Other embodiments provide the gene corresponding to the cDNA sequence of SEQ ID NO:8.

In other embodiments, the present invention provides a composition comprising a protein, wherein said protein comprises an amino acid sequence selected from the group consisting of:

(a) the amino acid sequence of SEQ ID NO:9;
(b) the amino acid sequence of SEQ ID NO:9 from amino acid 50 to amino acid 130;
(c) fragments of the amino acid sequence of SEQ ID NO:9; and
(d) the amino acid sequence encoded by the cDNA insert of clone BV239_2 deposited under accession number ATCC 98115; the protein being substantially free from other mammalian proteins. Preferably such protein comprises the amino acid sequence of SEQ ID NO:9 or the amino acid sequence of SEQ ID NO:9 from amino acid 50 to amino acid 130.

In one embodiment, the present invention provides a composition comprising an isolated polynucleotide selected from the group consisting of:

(a) a polynucleotide comprising the nucleotide sequence of SEQ ID NO:11;
(b) a polynucleotide comprising the nucleotide sequence of SEQ ID NO:11 from nucleotide 83 to nucleotide 307;
(c) a polynucleotide comprising the nucleotide sequence of the full length protein coding sequence of clone BL341_4 deposited under accession number ATCC 98115;
(d) a polynucleotide encoding the full length protein encoded by the cDNA insert of clone BL341_4 deposited under accession number ATCC 98115;
(e) a polynucleotide comprising the nucleotide sequence of the mature protein coding sequence of clone BL341_4 deposited under accession number ATCC 98115;
(f) a polynucleotide encoding the mature protein encoded by the cDNA insert of clone BL341_4 deposited under accession number ATCC 98115;
(g) a polynucleotide encoding a protein comprising the amino acid sequence of SEQ ID NO:12;
(h) a polynucleotide encoding a protein comprising a fragment of the amino acid sequence of SEQ ID NO:12 having biological activity;
(i) a polynucleotide which is an allelic variant of a polynucleotide of (a)–(d) above;
(j) a polynucleotide which encodes a species homologue of the protein of (g) or (h) above.

Preferably, such polynucleotide comprises the nucleotide sequence of SEQ ID NO:11 from nucleotide 83 to nucleotide 307; the nucleotide sequence of the full length protein coding sequence of clone BL341_4 deposited under accession number ATCC 98115; or the nucleotide sequence of the mature protein coding sequence of clone BL341_4 deposited under accession number ATCC 98115. In other preferred embodiments, the polynucleotide encodes the full length or mature protein encoded by the cDNA insert of clone BL341_4 deposited under accession number ATCC 98115. In yet other preferred embodiments, the present invention provides a polynucleotide encoding a protein comprising the amino acid sequence of SEQ ID NO: 12 from amino acid 7 to amino acid 65.

Other embodiments provide the gene corresponding to the cDNA sequence of SEQ ID NO:11 or SEQ ID NO:.

In other embodiments, the present invention provides a composition comprising a protein, wherein said protein comprises an amino acid sequence selected from the group consisting of:

(a) the amino acid sequence of SEQ ID NO:12;
(b) the amino acid sequence of SEQ ID NO:12 from amino acid 7 to amino acid 65;
(c) fragments of the amino acid sequence of SEQ ID NO:12; and
(d) the amino acid sequence encoded by the cDNA insert of clone BL341_4 deposited under accession number ATCC 98115; the protein being substantially free from other mammalian proteins. Preferably such protein comprises the amino acid sequence of SEQ ID NO:12 or the amino acid sequence of SEQ ID NO:12 from amino acid 7 to amino acid 65.

In one embodiment, the present invention provides a composition comprising an isolated polynucleotide selected from the group consisting of:

(a) a polynucleotide comprising the nucleotide sequence of SEQ ID:13;
(b) a polynucleotide comprising the nucleotide sequence of SEQ ID NO:13 from nucleotide 2 to nucleotide 415;
(c) a polynucleotide comprising the nucleotide sequence of the full length protein coding sequence of clone CC25_16 deposited under accession number ATCC 98115;
(d) a polynucleotide encoding the full length protein encoded by the cDNA insert of clone CC25_16 deposited under accession number ATCC 98115;
(e) a polynucleotide comprising the nucleotide sequence of the mature protein coding sequence of clone CC25_16 deposited under accession number ATCC 98115;
(f) a polynucleotide encoding the mature protein encoded by the cDNA insert of clone CC25_16 deposited under accession number ATCC 98115;
(g) a polynucleotide encoding a protein comprising the amino acid sequence of SEQ ID NO:14;
(h) a polynucleotide encoding a protein comprising a fragment of the amino acid sequence of SEQ ID NO:14 having biological activity;
(i) a polynucleotide which is an allelic variant of a polynucleotide of (a)–(d) above;
(j) a polynucleotide which encodes a species homologue of the protein of (g) or (h) above.

Preferably, such polynucleotide comprises the nucleotide sequence of SEQ ID NO:13 from nucleotide 2 to nucleotide 415; the nucleotide sequence of the full length protein coding sequence of clone CC25_16 deposited under accession number ATCC 98115; or the nucleotide sequence of the mature protein coding sequence of clone CC25_16 deposited under accession number ATCC 98115. In other preferred embodiments, the polynucleotide encodes the full length or mature protein encoded by the cDNA insert of clone CC25_16 deposited under accession number ATCC 98115. In yet other preferred embodiments, the present invention provides a polynucleotide encoding a protein comprising the amino acid sequence of SEQ ID NO:14 from amino acid 56 to amino acid 138.

Other embodiments provide the gene corresponding to the cDNA sequence of SEQ ID NO:13.

In other embodiments, the present invention provides a composition comprising a protein, wherein said protein comprises an amino acid sequence selected from the group consisting of:

(a) the amino acid sequence of SEQ ID NO:14;
(b) the amino acid sequence of SEQ ID NO:14 from amino acid 56 to amino acid 138;
(c) fragments of the amino acid sequence of SEQ ID NO:14; and
(d) the amino acid sequence encoded by the cDNA insert of clone CC25_16 deposited under accession number ATCC 98115; the protein being substantially free from other mammalian proteins. Preferably such protein comprises the amino acid sequence of SEQ ID NO:14 or the amino acid sequence of SEQ ID NO:14 from amino acid 56 to amino acid 138.

In one embodiment, the present invention provides a composition comprising an isolated polynucleotide selected from the group consisting of:

(a) a polynucleotide comprising the nucleotide sequence of SEQ ID NO:16;
(b) a polynucleotide comprising the nucleotide sequence of SEQ ID NO:16 from nucleotide 242 to nucleotide 322;
(c) a polynucleotide comprising the nucleotide sequence of the full length protein coding sequence of clone CC397_11 deposited under accession number ATCC 98115;
(d) a polynucleotide encoding the full length protein encoded by the cDNA insert of clone CC397_11 deposited under accession number ATCC 98115;
(e) a polynucleotide comprising the nucleotide sequence of the mature protein coding sequence of clone CC397_11 deposited under accession number ATCC 98115;
(f) a polynucleotide encoding the mature protein encoded by the cDNA insert of clone CC397_11 deposited under accession number ATCC 98115;
(g) a polynucleotide encoding a protein comprising the amino acid sequence of SEQ ID NO:17;
(h) a polynucleotide encoding a protein comprising a fragment of the amino acid sequence of SEQ ID NO:17 having biological activity;
(i) a polynucleotide which is an allelic variant of a polynucleotide of (a)–(d) above;
(j) a polynucleotide which encodes a species homologue of the protein of (g) or (h) above.

Preferably, such polynucleotide comprises the nucleotide sequence of SEQ ID NO:16 from nucleotide 242 to nucleotide 322; the nucleotide sequence of the full length protein coding sequence of clone CC397_11 deposited under accession number ATCC 98115; or the nucleotide sequence of the mature protein coding sequence of clone CC397_11 deposited under accession number ATCC 98115. In other preferred embodiments, the polynucleotide encodes the full length or mature protein encoded by the cDNA insert of clone CC397_11 deposited under accession number ATCC 98115.

Other embodiments provide the gene corresponding to the cDNA sequence of SEQ ID NO:16, SEQ ID NO:15 or SEQ ID NO:18.

In other embodiments, the present invention provides a composition comprising a protein, wherein said protein comprises an amino acid sequence selected from the group consisting of:

(a) the amino acid sequence of SEQ ID NO:17;

(b) fragments of the amino acid sequence of SEQ ID NO:17; and (c) the amino acid sequence encoded by the cDNA insert of clone CC397_11 deposited under accession number ATCC 98115; the protein being substantially free from other mammalian proteins. Preferably such protein comprises the amino acid sequence of SEQ ID NO:17.

In one embodiment, the present invention provides a composition comprising an isolated polynucleotide selected from the group consisting of:

(a) a polynucleotide comprising the nucleotide sequence of SEQ ID NO:20;

(b) a polynucleotide comprising the nucleotide sequence of SEQ ID NO:20 from nucleotide 253 to nucleotide 519;

(c) a polynucleotide comprising the nucleotide sequence of SEQ ID NO:20 from nucleotide 298 to nucleotide 519;

(d) a polynucleotide comprising the nucleotide sequence of the full length protein coding sequence of clone D305_2 deposited under accession number ATCC 98115;

(e) a polynucleotide encoding the full length protein encoded by the cDNA insert of clone D305_2 deposited under accession number ATCC 98115;

(f) a polynucleotide comprising the nucleotide sequence of the mature protein coding sequence of clone D305_2 deposited under accession number ATCC 98115;

(g) a polynucleotide encoding the mature protein encoded by the cDNA insert of clone D305_2 deposited under accession number ATCC 98115;

(h) a polynucleotide encoding a protein comprising the amino acid sequence of SEQ ID NO:21;

(i) a polynucleotide encoding a protein comprising a fragment of the amino acid sequence of SEQ ID NO:21 having biological activity;

(j) a polynucleotide which is an allelic variant of a polynucleotide of (a)–(g) above;

(k) a polynucleotide which encodes a species homologue of the protein of (h) or (i) above.

Preferably, such polynucleotide comprises the nucleotide sequence of SEQ ID NO:20 from nucleotide 253 to nucleotide 519; the nucleotide sequence of SEQ ID NO:20 from nucleotide 298 to nucleotide 519; the nucleotide sequence of the full length protein coding sequence of clone D305_2 deposited under accession number ATCC 98115; or the nucleotide sequence of the mature protein coding sequence of clone D305_2 deposited under accession number ATCC 98115. In other preferred embodiments, the polynucleotide encodes the full length or mature protein encoded by the cDNA insert of clone D305_2 deposited under accession number ATCC 98115.

Other embodiments provide the gene corresponding to the cDNA sequence of SEQ ID NO:20, SEQ ID NO:19 or SEQ ID NO:22.

In other embodiments, the present invention provides a composition comprising a protein, wherein said protein comprises an amino acid sequence selected from the group consisting of:

(a) the amino acid sequence of SEQ ID NO:21;

(b) fragments of the amino acid sequence of SEQ ID NO:21; and (c) the amino acid sequence encoded by the cDNA insert of clone D305_2 deposited under accession number ATCC 98115; the protein being substantially free from other mammalian proteins. Preferably such protein comprises the amino acid sequence of SEQ ID NO:21.

In one embodiment, the present invention provides a composition comprising an isolated polynucleotide selected from the group consisting of:

(a) a polynucleotide comprising the nucleotide sequence of SEQ ID NO:23;

(b) a polynucleotide comprising the nucleotide sequence of SEQ ID NO:23 from nucleotide 194 to nucleotide 622;

(c) a polynucleotide comprising the nucleotide sequence of SEQ ID NO:23 from nucleotide 524 to nucleotide 622;

(d) a polynucleotide comprising the nucleotide sequence of the full length protein coding sequence of clone G55_1 deposited under accession number ATCC 98115;

(e) a polynucleotide encoding the full length protein encoded by the cDNA insert of clone G55_1 deposited under accession number ATCC 98115;

(f) a polynucleotide comprising the nucleotide sequence of the mature protein coding sequence of clone G55_1 deposited under accession number ATCC 98115;

(g) a polynucleotide encoding the mature protein encoded by the cDNA insert of clone G55_1 deposited under accession number ATCC 98115;

(h) a polynucleotide encoding a protein comprising the amino acid sequence of SEQ ID NO:24;

(i) a polynucleotide encoding a protein comprising a fragment of the amino acid sequence of SEQ ID NO:24 having biological activity;

(j) a polynucleotide which is an allelic variant of a polynucleotide of (a)–(g) above;

(k) a polynucleotide which encodes a species homologue of the protein of (h) or (i) above.

Preferably, such polynucleotide comprises the nucleotide sequence of SEQ ID NO:23 from nucleotide 194 to nucleotide 622; the nucleotide sequence of SEQ ID NO:23 from nucleotide 524 to nucleotide 622; the nucleotide sequence of the full length protein coding sequence of clone G55_1 deposited under accession number ATCC 98115; or the nucleotide sequence of the mature protein coding sequence of clone G55_1 deposited under accession number ATCC 98115. In other preferred embodiments, the polynucleotide encodes the full length or mature protein encoded by the cDNA insert of clone G55_1 deposited under accession number ATCC 98115. In yet other preferred embodiments, the present invention provides a polynucleotide encoding a protein comprising the amino acid sequence of SEQ ID NO:24 from amino acid 1 to amino acid 32.

Other embodiments provide the gene corresponding to the cDNA sequence of SEQ ID NO:23 or SEQ ID NO:.

In other embodiments, the present invention provides a composition comprising a protein, wherein said protein comprises an amino acid sequence selected from the group consisting of:

(a) the amino acid sequence of SEQ ID NO:24;

(b) the amino acid sequence of SEQ ID NO:24 from amino acid 1 to amino acid 32;

(c) fragments of the amino acid sequence of SEQ ID NO:24; and (d) the amino acid sequence encoded by the cDNA insert of clone G55_1 deposited under accession number ATCC 98115; the protein being substantially free from other mammalian proteins. Preferably such protein comprises the amino acid sequence of SEQ ID NO:24 or the amino acid sequence of SEQ ID NO:24 from amino acid 1 to amino acid 32.

In one embodiment, the present invention provides a composition comprising an isolated polynucleotide selected from the group consisting of:

(a) a polynucleotide comprising the nucleotide sequence of SEQ ID NO:26;

(b) a polynucleotide comprising the nucleotide sequence of SEQ ID NO:26 from nucleotide 402 to nucleotide 533;

(c) a polynucleotide comprising the nucleotide sequence of SEQ ID NO:26 from nucleotide 447 to nucleotide 533;

(d) a polynucleotide comprising the nucleotide sequence of the full length protein coding sequence of clone K39_2 deposited under accession number ATCC 98115;

(e) a polynucleotide encoding the full length protein encoded by the cDNA insert of clone K39_2 deposited under accession number ATCC 98115;

(f) a polynucleotide comprising the nucleotide sequence of the mature protein coding sequence of clone K39_2 deposited under accession number ATCC 98115;

(g) a polynucleotide encoding the mature protein encoded by the cDNA insert of clone K39_2 deposited under accession number ATCC 98115;

(h) a polynucleotide encoding a protein comprising the amino acid sequence of SEQ ID NO:27;

(i) a polynucleotide encoding a protein comprising a fragment of the amino acid sequence of SEQ ID NO:27 having biological activity;

(j) a polynucleotide which is an allelic variant of a polynucleotide of (a)-(g) above;

(k) a polynucleotide which encodes a species homologue of the protein of (h) or (i) above.

Preferably, such polynucleotide comprises the nucleotide sequence of SEQ ID NO:26 from nucleotide 402 to nucleotide 533; the nucleotide sequence of SEQ ID NO:26 from nucleotide 447 to nucleotide 533; the nucleotide sequence of the full length protein coding sequence of clone K39_2 deposited under accession number ATCC 98115; or the nucleotide sequence of the mature protein coding sequence of clone K39_2 deposited under accession number ATCC 98115. In other preferred embodiments, the polynucleotide encodes the full length or mature protein encoded by the cDNA insert of clone K39_2 deposited under accession number ATCC 98115.

Other embodiments provide the gene corresponding to the cDNA sequence of SEQ ID NO:26 or SEQ ID NO:.

In other embodiments, the present invention provides a composition comprising a protein, wherein said protein comprises an amino acid sequence selected from the group consisting of:

(a) the amino acid sequence of SEQ ID NO:27;

(b) fragments of the amino acid sequence of SEQ ID NO:27; and (c) the amino acid sequence encoded by the cDNA insert of clone K39_2 deposited under accession number ATCC 98115; the protein being substantially free from other mammalian proteins. Preferably such protein comprises the amino acid sequence of SEQ ID NO:27.

In one embodiment, the present invention provides a composition comprising an isolated polynucleotide selected from the group consisting of:

(a) a polynucleotide comprising the nucleotide sequence of SEQ ID NO:29;

(b) a polynucleotide comprising the nucleotide sequence of SEQ ID NO:29 from nucleotide 241 to nucleotide 525;

(c) a polynucleotide comprising the nucleotide sequence of the full length protein coding sequence of clone K330_2 deposited under accession number ATCC 98115;

(d) a polynucleotide encoding the full length protein encoded by the cDNA insert of clone K330_2 deposited under accession number ATCC 98115;

(e) a polynucleotide comprising the nucleotide sequence of the mature protein coding sequence of clone K330_2 deposited under accession number ATCC 98115;

(f) a polynucleotide encoding the mature protein encoded by the cDNA insert of clone K330_2 deposited under accession number ATCC 98115;

(g) a polynucleotide encoding a protein comprising the amino acid sequence of SEQ ID NO:30;

(h) a polynucleotide encoding a protein comprising a fragment of the amino acid sequence of SEQ ID NO:30 having biological activity;

(i) a polynucleotide which is an allelic variant of a polynucleotide of (a)-(d) above;

(j) a polynucleotide which encodes a species homologue of the protein of (g) or (h) above.

Preferably, such polynucleotide comprises the nucleotide sequence of SEQ ID NO:29 from nucleotide 241 to nucleotide 525; the nucleotide sequence of the full length protein coding sequence of clone K330_2 deposited under accession number ATCC 98115; or the nucleotide sequence of the mature protein coding sequence of clone K330_2 deposited under accession number ATCC 98115. In other preferred embodiments, the polynucleotide encodes the full length or mature protein encoded by the cDNA insert of clone K330_2 deposited under accession number ATCC 98115. In yet other preferred embodiments, the present invention provides a polynucleotide encoding a protein comprising the amino acid sequence of SEQ ID NO:30 from amino acid 1 to amino acid 35.

Other embodiments provide the gene corresponding to the cDNA sequence of SEQ ID NO:29 or SEQ ID NO:.

In other embodiments, the present invention provides a composition comprising a protein, wherein said protein comprises an amino acid sequence selected from the group consisting of:

(a) the amino acid sequence of SEQ ID NO:30;

(b) the amino acid sequence of SEQ ID NO:30 from amino acid 1 to amino acid 35;

(c) fragments of the amino acid sequence of SEQ ID NO:30; and (d) the amino acid sequence encoded by the cDNA insert of clone K330_2 deposited under accession number ATCC 98115; the protein being substantially free from other mammalian proteins. Preferably such protein comprises the amino acid sequence of SEQ ID NO:30 or the amino acid sequence of SEQ ID NO:30 from amino acid 1 to amino acid 35.

In one embodiment, the present invention provides a composition comprising an isolated polynucleotide selected from the group consisting of:

(a) a polynucleotide comprising the nucleotide sequence of SEQ ID NO:32;

(b) a polynucleotide comprising the nucleotide sequence of SEQ ID NO:32 from nucleotide 158 to nucleotide 157;

(c) a polynucleotide comprising the nucleotide sequence of the full length protein coding sequence of clone K363_2 deposited under accession number ATCC 98115;

(d) a polynucleotide encoding the full length protein encoded by the cDNA insert of clone K363_2 deposited under accession number ATCC 98115;

(e) a polynucleotide comprising the nucleotide sequence of the mature protein coding sequence of clone K363_2 deposited under accession number ATCC 98115;

(f) a polynucleotide encoding the mature protein encoded by the cDNA insert of clone K363_2 deposited under accession number ATCC 98115;

(g) a polynucleotide encoding a protein comprising the amino acid sequence of SEQ ID NO:33;

(h) a polynucleotide encoding a protein comprising a fragment of the amino acid sequence of SEQ ID NO:33 having biological activity;

(i) a polynucleotide which is an allelic variant of a polynucleotide of (a)–(d) above;

(j) a polynucleotide which encodes a species homologue of the protein of (g) or (h) above.

Preferably, such polynucleotide comprises the nucleotide sequence of SEQ ID NO:32 from nucleotide 158 to nucleotide 571; the nucleotide sequence of the full length protein coding sequence of clone K363_2 deposited under accession number ATCC 98115; or the nucleotide sequence of the mature protein coding sequence of clone K363_2 deposited under accession number ATCC 98115. In other preferred embodiments, the polynucleotide encodes the full length or mature protein encoded by the cDNA insert of clone K363_2 deposited under accession number ATCC 98115. In yet other preferred embodiments, the present invention provides a polynucleotide encoding a protein comprising the amino acid sequence of SEQ ID NO:33 from amino acid 24 to amino acid 96.

Other embodiments provide the gene corresponding to the cDNA sequence of SEQ ID NO:32 or SEQ ID NO:.

In other embodiments, the present invention provides a composition comprising a protein, wherein said protein comprises an amino acid sequence selected from the group consisting of:

(a) the amino acid sequence of SEQ ID NO:33;

(b) the amino acid sequence of SEQ ID NO:33 from amino acid 24 to amino acid 96;

(c) fragments of the amino acid sequence of SEQ ID NO:33; and (d) the amino acid sequence encoded by the cDNA insert of clone K363_2 deposited under accession number ATCC 98115; the protein being substantially free from other mammalian proteins. Preferably such protein comprises the amino acid sequence of SEQ ID NO:33 or the amino acid sequence of SEQ ID NO:33 from amino acid 24 to amino acid 96.

In one embodiment, the present invention provides a composition comprising an isolated polynucleotide selected from the group consisting of:

(a) a polynucleotide comprising the nucleotide sequence of SEQ ID NO:35;

(b) a polynucleotide comprising the nucleotide sequence of SEQ ID NO:35 from nucleotide 401 to nucleotide 526;

(c) a polynucleotide comprising the nucleotide sequence of the full length protein coding sequence of clone K446_2 deposited under accession number ATCC 98115;

(d) a polynucleotide encoding the full length protein encoded by the cDNA insert of clone K446_2 deposited under accession number ATCC 98115;

(e) a polynucleotide comprising the nucleotide sequence of the mature protein coding sequence of clone K446_2 deposited under accession number ATCC 98115;

(f) a polynucleotide encoding the mature protein encoded by the cDNA insert of clone K446_2 deposited under accession number ATCC 98115;

(g) a polynucleotide encoding a protein comprising the amino acid sequence of SEQ ID NO:36;

(h) a polynucleotide encoding a protein comprising a fragment of the amino acid sequence of SEQ ID NO:36 having biological activity;

(i) a polynucleotide which is an allelic variant of a polynucleotide of (a)–(d) above;

(j) a polynucleotide which encodes a species homologue of the protein of (g) or (h) above.

Preferably, such polynucleotide comprises the nucleotide sequence of SEQ ID NO:35 from nucleotide 401 to nucleotide 526; the nucleotide sequence of the full length protein coding sequence of clone K446_2 deposited under accession number ATCC 98115; or the nucleotide sequence of the mature protein coding sequence of clone K446_2 deposited under accession number ATCC 98115. In other preferred embodiments, the polynucleotide encodes the full length or mature protein encoded by the cDNA insert of clone K446_2 deposited under accession number ATCC 98115.

Other embodiments provide the gene corresponding to the cDNA sequence of SEQ ID NO:35 or SEQ ID NO:.

In other embodiments, the present invention provides a composition comprising a protein, wherein said protein comprises an amino acid sequence selected from the group consisting of:

(a) the amino acid sequence of SEQ ID NO:36;

(b) fragments of the amino acid sequence of SEQ ID NO:36; and (c) the amino acid sequence encoded by the cDNA insert of clone K446_2 deposited under accession number ATCC 98115; the protein being substantially free from other mammalian proteins. Preferably such protein comprises the amino acid sequence of SEQ ID NO:36.

In one embodiment, the present invention provides a composition comprising an isolated polynucleotide selected from the group consisting of:

(a) a polynucleotide comprising the nucleotide sequence of SEQ ID NO:38;

(b) a polynucleotide comprising the nucleotide sequence of SEQ ID NO:38 from nucleotide 380 to nucleotide 535;

(c) a polynucleotide comprising the nucleotide sequence of the full length protein coding sequence of clone K464_3 deposited under accession number ATCC 98115;

(d) a polynucleotide encoding the full length protein encoded by the cDNA insert of clone K464_3 deposited under accession number ATCC 98115;

(e) a polynucleotide comprising the nucleotide sequence of the mature protein coding sequence of clone K464_3 deposited under accession number ATCC 98115;

(f) a polynucleotide encoding the mature protein encoded by the cDNA insert of clone K464_3 deposited under accession number ATCC 98115;

(g) a polynucleotide encoding a protein comprising the amino acid sequence of SEQ ID NO:39;

(h) a polynucleotide encoding a protein comprising a fragment of the amino acid sequence of SEQ ID NO:39 having biological activity;

(i) a polynucleotide which is an allelic variant of a polynucleotide of (a)–(d) above;

(j) a polynucleotide which encodes a species homologue of the protein of (g) or (h) above.

Preferably, such polynucleotide comprises the nucleotide sequence of SEQ ID NO:38 from nucleotide 380 to nucleotide 535; the nucleotide sequence of the full length protein coding sequence of clone K464_3 deposited under accession number ATCC 98115; or the nucleotide sequence of the mature protein coding sequence of clone K464_3 deposited under accession number ATCC 98115. In other preferred embodiments, the polynucleotide encodes the full length or mature protein encoded by the cDNA insert of clone K464_3 deposited under accession number ATCC 98115.

Other embodiments provide the gene corresponding to the cDNA sequence of SEQ ID NO:38 or SEQ ID NO:.

In other embodiments, the present invention provides a composition comprising a protein, wherein said protein comprises an amino acid sequence selected from the group consisting of:

(a) the amino acid sequence of SEQ ID NO:39;

(b) fragments of the amino acid sequence of SEQ ID NO:39; and (c) the amino acid sequence encoded by the cDNA insert of clone K464_3 deposited under accession number ATCC 98115; the protein being substantially free from other mammalian proteins. Preferably such protein comprises the amino acid sequence of SEQ ID NO:39.

In one embodiment, the present invention provides a composition comprising an isolated polynucleotide selected from the group consisting of:

(a) a polynucleotide comprising the nucleotide sequence of SEQ ID NO:41;

(b) a polynucleotide comprising the nucleotide sequence of SEQ ID NO:41 from nucleotide 221 to nucleotide 520;

(c) a polynucleotide comprising the nucleotide sequence of the full length protein coding sequence of clone K483_1 deposited under accession number ATCC 98115;

(d) a polynucleotide encoding the full length protein encoded by the cDNA insert of clone K483_1 deposited under accession number ATCC 98115;

(e) a polynucleotide comprising the nucleotide sequence of the mature protein coding sequence of clone K483_1 deposited under accession number ATCC 98115;

(f) a polynucleotide encoding the mature protein encoded by the cDNA insert of clone K483_1 deposited under accession number ATCC 98115;

(g) a polynucleotide encoding a protein comprising the amino acid sequence of SEQ ID NO:42;

(h) a polynucleotide encoding a protein comprising a fragment of the amino acid sequence of SEQ ID NO:42 having biological activity;

(i) a polynucleotide which is an allelic variant of a polynucleotide of (a)–(d) above;

(j) a polynucleotide which encodes a species homologue of the protein of (g) or (h) above.

Preferably, such polynucleotide comprises the nucleotide sequence of SEQ ID NO:41 from nucleotide 221 to nucleotide 520; the nucleotide sequence of the full length protein coding sequence of clone K483_1 deposited under accession number ATCC 98115; or the nucleotide sequence of the mature protein coding sequence of clone K483_1 deposited under accession number ATCC 98115. In other preferred embodiments, the polynucleotide encodes the full length or mature protein encoded by the cDNA insert of clone K483_1 deposited under accession number ATCC 98115.

Other embodiments provide the gene corresponding to the cDNA sequence of SEQ ID NO:41 or SEQ ID NO:.

In other embodiments, the present invention provides a composition comprising a protein, wherein said protein comprises an amino acid sequence selected from the group consisting of:

(a) the amino acid sequence of SEQ ID NO:42;

(b) fragments of the amino acid sequence of SEQ ID NO:42; and (c) the amino acid sequence encoded by the cDNA insert of clone K483_1 deposited under accession number ATCC 98115; the protein being substantially free from other mammalian proteins. Preferably such protein comprises the amino acid sequence of SEQ ID NO:42.

In one embodiment, the present invention provides a composition comprising an isolated polynucleotide selected from the group consisting of:

(a) a polynucleotide comprising the nucleotide sequence of SEQ ID NO:44;

(b) a polynucleotide comprising the nucleotide sequence of SEQ ID NO:44 from nucleotide 446 to nucleotide 835;

(c) a polynucleotide comprising the nucleotide sequence of SEQ ID NO:44 from nucleotide 503 to nucleotide 835;

(d) a polynucleotide comprising the nucleotide sequence of the full length protein coding sequence of clone L69_2 deposited under accession number ATCC 98115;

(e) a polynucleotide encoding the full length protein encoded by the cDNA insert of clone L69_2 deposited under accession number ATCC 98115;

(f) a polynucleotide comprising the nucleotide sequence of the mature protein coding sequence of clone L69_2 deposited under accession number ATCC 98115;

(g) a polynucleotide encoding the mature protein encoded by the cDNA insert of clone L69_2 deposited under accession number ATCC 98115;

(h) a polynucleotide encoding a protein comprising the amino acid sequence of SEQ ID NO:45;

(i) a polynucleotide encoding a protein comprising a fragment of the amino acid sequence of SEQ ID NO:45 having biological activity;

(j) a polynucleotide which is an allelic variant of a polynucleotide of (a)–(g) above;

(k) a polynucleotide which encodes a species homologue of the protein of (h) or (i) above.

Preferably, such polynucleotide comprises the nucleotide sequence of SEQ ID NO:44 from nucleotide 446 to nucleotide 835; the nucleotide sequence of SEQ ID NO:44 from nucleotide 503 to nucleotide 835; the nucleotide sequence of the full length protein coding sequence of clone L69_2 deposited under accession number ATCC 98115; or the nucleotide sequence of the mature protein coding sequence of clone L69_2 deposited under accession number ATCC 98115. In other preferred embodiments, the polynucleotide encodes the full length or mature protein encoded by the cDNA insert of clone L69_2 deposited under accession number ATCC 98115. In yet other preferred embodiments, the present invention provides a polynucleotide encoding a protein comprising the amino acid sequence of SEQ ID NO:45 from amino acid 1 to amino acid 93.

Other embodiments provide the gene corresponding to the cDNA sequence of SEQ ID NO:44 or SEQ ID NO:.

In other embodiments, the present invention provides a composition comprising a protein, wherein said protein comprises an amino acid sequence selected from the group consisting of:

(a) the amino acid sequence of SEQ ID NO:45;

(b) the amino acid sequence of SEQ ID NO:45 from amino acid 1 to amino acid 93;

(c) fragments of the amino acid sequence of SEQ ID NO:45; and (d) the amino acid sequence encoded by the cDNA insert of clone L69_2 deposited under accession number ATCC 98115; the protein being substantially free from other mammalian proteins. Preferably such protein comprises the amino acid sequence of SEQ ID NO:45 or the amino acid sequence of SEQ ID NO:45 from amino acid 1 to amino acid 93.

In one embodiment, the present invention provides a composition comprising an isolated polynucleotide selected from the group consisting of:

(a) a polynucleotide comprising the nucleotide sequence of SEQ ID NO:48;

(b) a polynucleotide comprising the nucleotide sequence of SEQ ID NO:48 from nucleotide 342 to nucleotide 542;

(c) a polynucleotide comprising the nucleotide sequence of SEQ ID NO:48 from nucleotide 402 to nucleotide 542;

(d) a polynucleotide comprising the nucleotide sequence of the full length protein coding sequence of clone AJ172_2 deposited under accession number ATCC 98115;

(e) a polynucleotide encoding the full length protein encoded by the cDNA insert of clone AJ172_2 deposited under accession number ATCC 98115;

(f) a polynucleotide comprising the nucleotide sequence of the mature protein coding sequence of clone AJ172_2 deposited under accession number ATCC 98115;

(g) a polynucleotide encoding the mature protein encoded by the cDNA insert of clone AJ172_2 deposited under accession number ATCC 98115;

(h) a polynucleotide encoding a protein comprising the amino acid sequence of SEQ ID NO:49;

(i) a polynucleotide encoding a protein comprising a fragment of the amino acid sequence of SEQ ID NO:49 having biological activity;

(j) a polynucleotide which is an allelic variant of a polynucleotide of (a)–(g) above;

(k) a polynucleotide which encodes a species homologue of the protein of (h) or (i) above.

Preferably, such polynucleotide comprises the nucleotide sequence of SEQ ID NO:48 from nucleotide 342 to nucleotide 542; the nucleotide sequence of SEQ ID NO:48 from nucleotide 402 to nucleotide 542; the nucleotide sequence of the full length protein coding sequence of clone AJ172_2 deposited under accession number ATCC 98115; or the nucleotide sequence of the mature protein coding sequence of clone AJ172_2 deposited under accession number ATCC 98115. In other preferred embodiments, the polynucleotide encodes the full length or mature protein encoded by the cDNA insert of clone AJ172_2 deposited under accession number ATCC 98115.

Other embodiments provide the gene corresponding to the cDNA sequence of SEQ ID NO:48, SEQ ID NO:47 or SEQ ID NO:50.

In other embodiments, the present invention provides a composition comprising a protein, wherein said protein comprises an amino acid sequence selected from the group consisting of:

(a) the amino acid sequence of SEQ ID NO:49;

(b) fragments of the amino acid sequence of SEQ ID NO:49; and (c) the amino acid sequence encoded by the cDNA insert of clone AJ172_2 deposited under accession number ATCC 98115; the protein being substantially free from other mammalian proteins. Preferably such protein comprises the amino acid sequence of SEQ ID NO:49.

In one embodiment, the present invention provides a composition comprising an isolated polynucleotide selected from the group consisting of:

(a) a polynucleotide comprising the nucleotide sequence of SEQ ID NO:52;

(b) a polynucleotide comprising the nucleotide sequence of SEQ ID NO:52 from nucleotide 185 to nucleotide 387;

(c) a polynucleotide comprising the nucleotide sequence of the full length protein coding sequence of clone AP224_2 deposited under accession number ATCC 98115;

(d) a polynucleotide encoding the full length protein encoded by the cDNA insert of clone AP224_2 deposited under accession number ATCC 98115;

(e) a polynucleotide comprising the nucleotide sequence of the mature protein coding sequence of clone AP224_2 deposited under accession number ATCC 98115;

(f) a polynucleotide encoding the mature protein encoded by the cDNA insert of clone AP224_2 deposited under accession number ATCC 98115;

(g) a polynucleotide encoding a protein comprising the amino acid sequence of SEQ ID NO:53;

(h) a polynucleotide encoding a protein comprising a fragment of the amino acid sequence of SEQ ID NO:53 having biological activity;

(i) a polynucleotide which is an allelic variant of a polynucleotide of (a)–(d) above;

(j) a polynucleotide which encodes a species homologue of the protein of (g) or (h) above.

Preferably, such polynucleotide comprises the nucleotide sequence of SEQ ID NO:52 from nucleotide 185 to nucleotide 387; the nucleotide sequence of the full length protein coding sequence of clone AP224_2 deposited under accession number ATCC 98115; or the nucleotide sequence of the mature protein coding sequence of clone AP224_2 deposited under accession number ATCC 98115. In other preferred embodiments, the polynucleotide encodes the full length or mature protein encoded by the cDNA insert of clone AP224_2 deposited under accession number ATCC 98115. In yet other preferred embodiments, the present invention provides a polynucleotide encoding a protein comprising the amino acid sequence of SEQ ID NO:53 from amino acid 1 to amino acid 28.

Other embodiments provide the gene corresponding to the cDNA sequence of SEQ ID NO:52, SEQ ID NO:51 or SEQ ID NO:54.

In other embodiments, the present invention provides a composition comprising a protein, wherein said protein comprises an amino acid sequence selected from the group consisting of:

(a) the amino acid sequence of SEQ ID NO:53;

(b) the amino acid sequence of SEQ ID NO:53 from amino acid 1 to amino acid 28;

(c) fragments of the amino acid sequence of SEQ ID NO:53; and (d) the amino acid sequence encoded by the cDNA insert of clone AP224_2 deposited under accession number ATCC 98115; the protein being substantially free from other mammalian proteins. Preferably such protein comprises the amino acid sequence of SEQ ID NO:53 or the amino acid sequence of SEQ ID NO:53 from amino acid 1 to amino acid 28.

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing a protein, which comprise:

(a) growing a culture of the host cell transformed with such polynucleotide compositions in a suitable culture medium; and (b) purifying the protein from the culture.

The protein produced according to such methods is also provided by the present invention. Preferred embodiments include those in which the protein produced by such process is a mature form of the protein.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

DETAILED DESCRIPTION

Isolated Proteins and Polynucleotides

Nucleotide and amino acid sequences are reported below for each clone and protein disclosed in the present application. In some instances the sequences are preliminary and may include some incorrect or ambiguous bases or amino acids. The actual nucleotide sequence of each clone can readily be determined by sequencing of the deposited clone in accordance with known methods. The predicted amino acid sequence (both full length and mature) can then be determined from such nucleotide sequence. The amino acid sequence of the protein encoded by a particular clone can also be determined by expression of the clone in a suitable host cell, collecting the protein and determining its sequence.

For each disclosed protein applicants have identified what they have determined to be the reading frame best identifiable with sequence information available at the time of filing. Because of the partial ambiguity in reported sequence information, reported protein sequences include "Xaa" designators. These "Xaa" designators indicate either (1) a residue which cannot be identified because of nucleotide sequence ambiguity or (2) a stop codon in the determined nucleotide sequence where applicants believe one should not exist (if the nucleotide sequence were determined more accurately).

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Clone "AJ26_3"

A polynucleotide of the present invention has been identified as clone "AJ26_3". AJ26_3 was isolated from a human adult testes cDNA library using methods which are selective for cDNAs encoding secreted proteins. AJ26_3 is a full-length clone, including the entire coding sequence of a secreted protein (also referred to herein as "AJ26_3 protein").

The nucleotide sequence of the 5' portion of AJ26_3 as presently determined is reported in SEQ ID NO1. What applicants presently believe is the proper reading frame for the coding region is indicated in SEQ ID NO:2. The predicted acid sequence of the AJ26_3 protein corresponding to the foregoing nucleotide sequence is reported in SEQ ID NO:2. Additional nucleotide sequence from the 3' portion of AJ26_3, including the polyA tail, is reported in SEQ ID NO:3.

The EcoRI/NotI restriction fragment obtainable from the deposit containing clone AJ26_3 should be approximately 2320 bp.

The nucleotide sequence disclosed herein for AJ26_3 was searched against the GenBank database using BLASTA/BLASTX and FASTA search protocols. AJ26_3 demonstrated at least some homology with Xenopus CTX protein (U43394, J01917, BlastX). Based upon homology, AJ26_3 proteins and each homologous protein or peptide may share at least some activity.

Clone "BL89_10"

A polynucleotide of the present invention has been identified as clone "BL89_10". BL89_10 was isolated from a human adult testes cDNA library using methods which are selective for cDNAs encoding secreted proteins. BL89_10 is a full-length clone, including the entire coding sequence of a secreted protein (also referred to herein as "BL89_10 protein").

The nucleotide sequence of the 5' portion of BL89_10 as presently determined is reported in SEQ ID NO:4. An additional internal nucleotide sequence from BL89_10 as presently determined is reported in SEQ ID NO:5. What applicants believe is the proper reading frame and the predicted amino acid sequence encoded by such internal sequence is reported in SEQ ID NO:6. Additional nucleotide sequence from the 3' portion of BL89_10, including the polyA tail, is reported in SEQ ID NO:7.

The EcoRI/NotI restriction fragment obtainable from the deposit containing clone BL89_10 should be approximately 3290 bp.

The nucleotide sequence disclosed herein for BL89_10 was searched against the GenBank database using BLASTA/BLASTX and FASTA search protocols. No hits were found in the database.

Clone "BV239_2"

A polynucleotide of the present invention has been identified as clone "BV239_2". BV239_2 was isolated from a human adult brain cDNA library using methods which are selective for cDNAs encoding secreted proteins. BV239_2 is a full-length clone, including the entire coding sequence of a secreted protein (also referred to herein as "BV239_2 protein").

The nucleotide sequence of BV239_2 as presently determined is reported in SEQ ID NO:8. What applicants presently believe to be the proper reading frame and the predicted amino acid sequence of the BV239_2 protein corresponding to the foregoing nucleotide sequence is reported in SEQ ID NO:9.

The EcoRI/NotI restriction fragment obtainable from the deposit containing clone BV239_2 should be approximately 300 bp.

The nucleotide sequence disclosed herein for BV239_2 was searched against the GenBank database using BLASTA/BLASTX and FASTA search protocols. No hits were found in the database.

Clone "BL341 4"

A polynucleotide of the present invention has been identified as clone "BL341_4". BL341_4 was isolated from a human adult testes cDNA library using methods which are selective for cDNAs encoding secreted proteins. BL341_4 is a full-length clone, including the entire coding sequence of a secreted protein (also referred to herein as "BL341_4 protein").

The partial nucleotide sequence of BL341_4, including its 3' end and any identified polA tail, as presently determined is reported in SEQ ID NO:11. What applicants presently believe is the proper reading frame for the coding region is indicated in SEQ ID NO:12. The predicted acid sequence of the BL341_4 protein corresponding to the foregoing nucleotide sequence is reported in SEQ ID NO:12. Additional nucleotide sequence from the 5' portion of BL341_4 is reported in SEQ ID NO:10.

The EcoRI/NotI restriction fragment obtainable from the deposit containing clone BL341_4 should be approximately 600 bp.

The nucleotide sequence disclosed herein for BL341_4 was searched against the GenBank database using BLASTA/BLASTX and FASTA search protocols. No hits were found in the database.

Clone "CC25 16"

A polynucleotide of the present invention has been identified as clone "CC25_16". CC25_16 was isolated from a human adult brain cDNA library using methods which are selective for cDNAs encoding secreted proteins. CC25_16 is a full-length clone, including the entire coding sequence of a secreted protein (also referred to herein as "CC25_16 protein").

The nucleotide sequence of CC25_16 as presently determined is reported in SEQ ID NO:13. What applicants presently believe to be the proper reading frame and the predicted amino acid sequence of the CC25_16 protein corresponding to the foregoing nucleotide sequence is reported in SEQ ID NO:14.

The EcoRI/NotI restriction fragment obtainable from the deposit containing clone CC25_16 should be approximately 280 bp.

The nucleotide sequence disclosed herein for CC25_16 was searched against the GenBank database using BLASTA/BLASTX and FASTA search protocols. No hits were found in the database.

Clone "CC397 11"

A polynucleotide of the present invention has been identified as clone "CC397_11". CC397_11 was isolated from a human adult brain cDNA library using methods which are selective for cDNAs encoding secreted proteins. CC397_11 is a full-length clone, including the entire coding sequence of a secreted protein (also referred to herein as "CC397_11 protein").

The nucleotide sequence of the 5' portion of CC397_11 as presently determined is reported in SEQ ID NO:15. An additional internal nucleotide sequence from CC397_11 as presently determined is reported in SEQ ID NO:16. What applicants believe is the proper reading frame and the predicted amino acid sequence encoded by such internal sequence is reported in SEQ ID NO:17. Additional nucleotide sequence from the 3' portion of CC397_11, including the polyA tail, is reported in SEQ ID NO:18.

The EcoRI/NotI restriction fragment obtainable from the deposit containing clone CC397_11 should be approximately 2300 bp.

The nucleotide sequence disclosed herein for CC397_11 was searched against the GenBank database using BLASTA/BLASTX and FASTA search protocols. No hits were found in the database.

Clone "D305 2"

A polynucleotide of the present invention has been identified as clone "D305_2". D305_2 was isolated from a human PBMC cDNA library using methods which are selective for cDNAs encoding secreted proteins. D305_2 is a full-length clone, including the entire coding sequence of a secreted protein (also referred to herein as "D305_2 protein").

The nucleotide sequence of the 5' portion of D305_2 as presently determined is reported in SEQ ID NO:19. An additional internal nucleotide sequence from D305_2 as presently determined is reported in SEQ ID NO:20. What applicants believe is the proper reading frame and the predicted amino acid sequence encoded by such internal sequence is reported in SEQ ID NO:21. Amino acids 1 to 15 of SEQ ID NO:21 are a predicted leader/signal sequence, with the predicted mature amino acid sequence beginning at amino acid 16. Additional nucleotide sequence from the 3' portion of D305_2, including the polyA tail, is reported in SEQ ID NO:22.

The nucleotide sequence disclosed herein for D305_2 was searched against the GenBank database using BLASTA/BLASTX and FASTA search protocols. D305_2 demonstrated at least some homology with an EST identified as "yi14g05.s1 Homo sapiens cDNA clone 139526 3'" (R68684, BlastN). Based upon homology, D305_2 proteins and each homologous protein or peptide may share at least some activity.

Clone "G55 1"

A polynucleotide of the present invention has been identified as clone "G55_1"G55_1 was isolated from a human PBMC cDNA library using methods which are selective for cDNAs encoding secreted proteins. G55_1 is a full-length clone, including the entire coding sequence of a secreted protein (also referred to herein as "G55_1 protein").

The nucleotide sequence of the 5' portion of G55_1 as presently determined is reported in SEQ ID NO:23. What applicants presently believe is the proper reading frame for the coding region is indicated in SEQ ID NO:24. The predicted acid sequence of the G55_1 protein corresponding to the foregoing nucleotide sequence is reported in SEQ ID NO:24. Amino acids 1 to 110 are the predicted leader/signal sequence, with the predicted mature amino acid sequence beginning at amino acid 111. Additional nucleotide sequence from the 3' portion of G55_1, including the polyA tail, is reported in SEQ ID NO:25.

The nucleotide sequence disclosed herein for G55_1 was searched against the GenBank database using BLASTA/BLASTX and FASTA search protocols. G55_1 demonstrated at least some identity with an EST identified as "yp16a07.r1 Homo sapiens cDNA clone 187572 5'" (R83586, BlastN). Based upon identity, G55_1 proteins and each identical protein or peptide may share at least some activity.

Clone "K39 2"

A polynucleotide of the present invention has been identified as clone "K39_2". K39_2 was isolated from a murine bone marrow (stromal cell line FCM-4) cDNA library using methods which are selective for cDNAs encoding secreted proteins. K39_2 is a full-length clone, including the entire coding sequence of a secreted protein (also referred to herein as "K39_2 protein").

The nucleotide sequence of the 5' portion of K39_2 as presently determined is reported in SEQ ID NO:26. What applicants presently believe is the proper reading frame for the coding region is indicated in SEQ ID NO:27. The predicted acid sequence of the K39_2 protein corresponding to the foregoing nucleotide sequence is reported in SEQ ID NO:27. Amino acids 1 to 15 are the predicted leader/signal sequence, with the predicted mature amino acid sequence beginning at amino acid 16. Additional nucleotide sequence from the 3' portion of K39_2, including the polyA tail, is reported in SEQ ID NO:28.

The EcoRI/NotI restriction fragment obtainable from the deposit containing clone K39_2 should be approximately 1675 bp.

The nucleotide sequence disclosed herein for K39_2 was searched against the GenBank database using BLASTA/BLASTX and FASTA search protocols. K39_2 demonstrated at least some identity with an EST identified as "Mouse 3'-directed cDNA MUSGS01125, clone Mc0564" (D18935, BlastN). Based upon identity, K39_2 proteins and each identical protein or peptide may share at least some activity.

Clone "K330 2"

A polynucleotide of the present invention has been identified as clone "K330_2". K330_2 was isolated from a murine bone marrow (stromal cell line FCM-4) cDNA library using methods which are selective for cDNAs encoding secreted proteins. K330_2 is a full-length clone, including the entire coding sequence of a secreted protein (also referred to herein as "K330_2 protein").

The nucleotide sequence of the 5' portion of K330_2 as presently determined is reported in SEQ ID NO:29. What applicants presently believe is the proper reading frame for the coding region is indicated in SEQ ID NO:30. The predicted acid sequence of the K330_2 protein corresponding to the foregoing nucleotide sequence is reported in SEQ ID NO:30. Additional nucleotide sequence from the 3' portion of K330_2, including the polyA tail, is reported in SEQ ID NO:31.

The EcoRI/NotI restriction fragment obtainable from the deposit containing clone K330_2 should be approximately 1300 bp.

The nucleotide sequence disclosed herein for K330_2 was searched against the GenBank database using BLASTA/BLASTX and FASTA search protocols. K330_2 demonstrated at least some homology with an EST identified as "yf82c07.s1 Homo sapiens cDNA clone 28939 3'" (R40824, BlastN). Based upon homology, K330_2 proteins and each homologous protein or peptide may share at least some activity.

Clone "K363 2"

A polynucleotide of the present invention has been identified as clone "K363_2". K363_2 was isolated from a murine bone marrow (stromal cell line FCM-4) cDNA library using methods which are selective for cDNAs encoding secreted proteins. K363_2 is a full-length clone, including the entire coding sequence of a secreted protein (also referred to herein as "K363_2 protein").

The nucleotide sequence of the 5' portion of K363_2 as presently determined is reported in SEQ ID NO:32. What applicants presently believe is the proper reading frame for the coding region is indicated in SEQ ID NO:33. The predicted acid sequence of the K363_2 protein corresponding to the foregoing nucleotide sequence is reported in SEQ ID NO:33. Additional nucleotide sequence from the '' portion of K363_2, including the polyA tail, is reported in SEQ ID NO:34.

The nucleotide sequence disclosed herein for K363_2 was searched against the GenBank database using BLASTA/BLASTX and FASTA search protocols. K363_2 demonstrated at least some homology with a sequence identified as "mouse embryonal carcinoma cell line DNA 67F09" (D21554, BlastN). Based upon homology, K363_2 proteins and each homologous protein or peptide may share at least some activity.

Clone "K446 2"

A polynucleotide of the present invention has been identified as clone "K446_2". K446_2 was isolated from a murine bone marrow (stromal cell line FCM-4) cDNA library using methods which are selective for cDNAs encoding secreted proteins. K446_2 is a full-length clone, including the entire coding sequence of a secreted protein (also referred to herein as "K446_2 protein").

The nucleotide sequence of the 5' portion of K446_2 as presently determined is reported in SEQ ID NO:35. What applicants presently believe is the proper reading frame for the coding region is indicated in SEQ ID NO:36. The predicted acid sequence of the K446_2 protein corresponding to the foregoing nucleotide sequence is reported in SEQ ID NO:36. Additional nucleotide sequence from the 3' portion of K446_2, including the polyA tail, is reported in SEQ ID NO:37.

The EcoRI/NotI restriction fragment obtainable from the deposit containing clone K446_2 should be approximately 800 bp.

The nucleotide sequence disclosed herein for K446_2 was searched against the GenBank database using BLASTA/BLASTX and FASTA search protocols. No hits were found in the database.

Clone "K464 3"

A polynucleotide of the present invention has been identified as clone "K464_3". K464_3 was isolated from a murine bone marrow (stromal cell line FCM-4) cDNA library using methods which are selective for cDNAs encoding secreted proteins. K464_3 is a full-length clone, including the entire coding sequence of a secreted protein (also referred to herein as "K464_3 protein").

The nucleotide sequence of the 5' portion of K464_3 as presently determined is reported in SEQ ID NO:38. What applicants presently believe is the proper reading frame for the coding region is indicated in SEQ ID NO:39. The predicted acid sequence of the K464_3 protein corresponding to the foregoing nucleotide sequence is reported in SEQ ID NO:39. Additional nucleotide sequence from the 3' portion of K464_3, including the polyA tail, is reported in SEQ ID NO:40.

The EcoRI/NotI restriction fragment obtainable from the deposit containing clone K464_3 should be approximately 750 bp.

The nucleotide sequence disclosed herein for K464_3 was searched against the GenBank database using BLASTA/BLASTX and FASTA search protocols. K464_3 demonstrated at least some homology with the following sequences: MHC T7 class I antigen (X16213, BlastX); murine cytotoxic T lymphocyte-specific serine protease (M22527, BlastN); an EST identified as "zc066b11.s1 Soares parathyroid tumor NbHPA Homo sapiens" (W32699, BlastN); and an EST identified as "mb82b10.r1 Soares mouse p3NMF19.5 Mus musculus cDNA clone 335899" (W36926, Fasta). Based upon homology, K464_3 proteins and each homologous protein or peptide may share at least some activity.

Clone "K483_1"

A polynucleotide of the present invention has been identified as clone "K483_1"K483_1 was isolated from a murine bone marrow (stromal cell line FCM-4) cDNA library using methods which are selective for cDNAs encoding secreted proteins. K483_1 is a full-length clone, including the entire coding sequence of a secreted protein (also referred to herein as "K483_1 protein").

The nucleotide sequence of the 5' portion of K483_1 as presently determined is reported in SEQ ID NO:41. What applicants presently believe is the proper reading frame for the coding region is indicated in SEQ ID NO:42. The predicted acid sequence of the K483_1 protein corresponding to the foregoing nucleotide sequence is reported in SEQ ID NO:42. Additional nucleotide sequence from the 3' portion of K483_1, including the polyA tail, is reported in SEQ ID NO:43.

The EcoRI/NotI restriction fragment obtainable from the deposit containing clone K483_1 should be approximately 1500 bp.

The nucleotide sequence disclosed herein for K483_1 was searched against the GenBank database using BLASTA/BLASTX and FASTA search protocols. K483_1 demonstrated at least some homology with an EST identified as "yw86b03.r1 Homo sapiens cDNA clone 259085 5'" (N41895, BlastN). Based upon homology, K483_1 proteins and each homologous protein or peptide may share at least some activity.

Clone "L69_2"

A polynucleotide of the present invention has been identified as clone "L69_2". L69_2 was isolated from a murine adult thymus cDNA library using methods which are selective for cDNAs encoding secreted proteins. L69_2 is a full-length clone, including the entire coding sequence of a secreted protein (also referred to herein as "L69_2 protein").

The nucleotide sequence of the 5' portion of L69_2 as presently determined is reported in SEQ ID NO:44. What applicants presently believe is the proper reading frame for the coding region is indicated in SEQ ID NO:45. The predicted acid sequence of the L69_2 protein corresponding to the foregoing nucleotide sequence is reported in SEQ ID NO:45. Amino acids 1 to 19 are the predicted leader/signal sequence, with the predicted mature amino acid sequence beginning at amino acid 20. Additional nucleotide sequence from the 3' portion of L69_2, including the polyA tail, is reported in SEQ ID NO:46.

The EcoRI/NotI restriction fragment obtainable from the deposit containing clone L69_2 should be approximately 1200 bp.

The nucleotide sequence disclosed herein for L69_2 was searched against the GenBank database using BLASTA/BLASTX and FASTA search protocols. L69_2 demonstrated at least some homology with the following sequences: human tissue specific secretory protein (A18921, BlastX; X67698, BlastN) and an EST identified as "md91b10.r1 Soares mouse embryo NbME13.5 14.5 Mus musculus" (W74864, BlastN). Based upon homology, L69_2 proteins and each homologous protein or peptide may share at least some activity.

Clone "AJ172_2"

A polynucleotide of the present invention has been identified as clone "AJ172_2". AJ172_2 was isolated from a human adult testes cDNA library using methods which are selective for cDNAs encoding secreted proteins. AJ172_2 is a full-length clone, including the entire coding sequence of a secreted protein (also referred to herein as "AJ172_2 protein").

The nucleotide sequence of the 5' portion of AJ172_2 as presently determined is reported in SEQ ID NO:47. An additional integral nucleotide sequence from AJ172_2 as presently determined is reported in SEQ ID NO:48. What applicants believe is the proper reading frame and the predicted amino acid sequence encoded by such internal sequence is reported in SEQ ID NO:49. Amino acids 1 to 20 of SEQ ID NO:49 are a predicted leader/signal sequence, with the predicted mature amino acid sequence beginning at amino acid 21. Additional nucleotide sequence from the 3' portion of AJ172_2, including the polyA tail, is reported in SEQ ID NO:50.

The EcoRI/NotI restriction fragment obtainable from the deposit containing clone AJ172_2 should be approximately 2700 bp.

The nucleotide sequence disclosed herein for AJ172_2 was searched against the GenBank database using BLASTA/BLASTX and FASTA search protocols. AJ172_2 demonstrated at least some homology with the following sequences: Friend murine leukemiz virus (M93134, BlastX); Moloney murine leukemia virus genome (J02255, BlastN); pol protein, Gibbon leukemia virus (M26927, BlastX); and EST identified as "yh46a09.s1 Homo sapiens cDNA clone 132760 3'" (R27389, BlastN). Based upon homology, AJ172_2 proteins and each homologous protein or peptide may share at least some activity.

Clone "AP224_2"

A polynucleotide of the present invention has been identified as clone "AP224_2". AP224_2 was isolated from a human adult placenta cDNA library using methods which are selective for cDNAs encoding secreted proteins. AP224_2 is a full-length clone, including the entire coding sequence of a secreted protein (also referred to herein as "AP224_2 protein").

The nucleotide sequence of the 5' portion of AP224_2 as presently determined is reported in SEQ ID NO:51. An additional internal nucleotide sequence from AP224_2 as presently determined is reported in SEQ ID NO:52. What applicants believe is the proper reading frame and the predicted amino acid sequence encoded by such internal sequence is reported in SEQ ID NO:53. Additional nucleotide sequence from the 3' portion of AP224_2, including the polyA tail, is reported in SEQ ID NO:54.

The EcoRI/NotI restriction fragment obtainable from the deposit containing clone AP224_2 should be approximately 2100 bp.

The nucleotide sequence disclosed herein for AP224_2 was searched against the GenBank database using BLASTA/BLASTX and FASTA search protocols. AP224_2 demonstrated at least some identity with an EST identified as "yf61f08.s1 Homo sapiens cDNA clone 26687 3'" (R37675, BlastN). Based upon identity, AP224_2 proteins and each identical protein or peptide may share at least some activity.

Deposit of Clones

Clones AJ26_3, BL89_10, BV239_2, BL341_4, CC25_16, CC397_11, D305_2, G55_1, K39_2, K330_2, K363_2, K446_2, K464_3, K483_1, L69_2, AJ172_2, and AP224_2 were deposited on Jul. 25, 1996 with the American Type Culture Collection under accession number ATCC 98115, from which each clone comprising a particular polynucleotide is obtainable. Each clone has been transfected into separate bacterial cells (*E. coli*) in this composite deposit. Each clone can be removed from the vector in which it was deposited by performing an EcoRI/NotI digestion (5' cite, EcoRI; 3' cite, NotI) to produce the appropriately sized fragment for such clone (approximate clone size fragment are identified below). Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The sequence of the oligonucleotide probe that was used to isolate each full-length clone is identified below, and should be most reliable in isolating the clone of interest.

| Clone | Probe Sequence |
|---|---|
| AJ26_3 | SEQ ID NO:55 |
| BL89_10 | SEQ ID NO:56 |
| BV239_2 | SEQ ID NO:57 |
| BL341_4 | SEQ ID NO:58 |
| CC25_16 | SEQ ID NO:59 |
| CC397_11 | SEQ ID NO:60 |
| D305_2 | SEQ ID NO:61 |
| G55_1 | SEQ ID NO:62 |
| K39_2 | SEQ ID NO:63 |
| K330_2 | SEQ ID NO:64 |
| K363_2 | SEQ ID NO:65 |
| K446_2 | SEQ ID NO:66 |
| K464_3 | SEQ ID NO:67 |
| K483_1 | SEQ ID NO:68 |
| L69_2 | SEQ ID NO:69 |
| AJ172_2 | SEQ ID NO:70 |
| AP224_2 | SEQ ID NO:71 |

In the sequences listed above which include an N at position 2, that position is occupied in preferred probes/primers by a biotinylated phosphoaramidite residue rather than a nucleotide (such as, for example, that produced by use of biotin phosphoramidite (1-dimethoxytrityloxy-2-(N-biotinyl-4-aminobutyl)-propyl-3-O-(2-cyanoethyl)-(N,N-diisopropyl)-(phosphoramadite) (Glen Research, cat. no. 10-1953)).

The design of the oligonucleotide probe should preferably follow these parameters:

(a) It should be designed to an area of the sequence which has the fewest ambiguous bases ("N's"), if any;

(b) It should be designed to have a $T_m$ of approx. 80° C. (assuming 2° for each A or T and 4 degrees for each G or C). The oligonucleotide should preferably be labeled with g-$^{32}$p ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/pmole.

The bacterial culture containing the pool of full-length clones should preferably be thawed and 100 µl of the stock used to inoculate a sterile culture flask containing 25 ml of sterile L-broth containing ampicillin at 100 µg/mL. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 µg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6×SSC (20×stock is 175.3 g NaCl/liter, 88.2 g Na citrate/liter, adjusted to pH 7.0 with NaOH) containing 0.5% SDS, 100 µg/ml of yeast RNA, and 10 mM EDTA (approximately 10 mL per 150 mm filter). Preferably, the probe is then added to the hybridization mix at a concentration greater than or equal to 1e+6 dpm/mL. The filter is then preferably incubated at 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al, J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form of such protein may be obtained by expression of the disclosed full-length polynucleotide (preferably those deposited with ATCC) in a suitable mammalian cell or other host cell. The sequence of the mature form of the protein may also be determinable from the amino acid sequence of the full-length form.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Species homologs of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No. 1555* (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of matlose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

Uses and Biological Activity

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without
 limitation those described in: Current Protocols in Immunology, Ed by J. E. Coilgan, A. M. Kruisbeek, D. H. Marguiles, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnoili et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994;

and Measurement of mouse and human Interferon γ, Schreiber, R. D. In *Current Protocols in Immunology*. J. E. e.a. Coiligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In *Current Protocols in Immunology*. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6-Nordan, R. In *Current Protocols in Immunology*. J. E. e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11-Bennett, F., Giannotti, J., Clark, S. C. and Turner, K. J. In *Current Protocols in Immunology*. J. E. e.a. Coligan eds. Vol 1 pp. 6.15.1 John Wiley and Sons, Toronto. 1991; Measurement of mouse and human Interleukin 9-Ciarletta, A., Giannotti, J., Clark, S. C. and Turner, K. J. In *Current Protocols in Immunology*. J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Marguiles, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by vital (e.g., HIV) as well as bacterial or fungal infections, or may result from autoimmune disorders. More specifically, infectious diseases causes by vital, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic vital diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-vital immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Marguiles, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coilgan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155: 111–122, 1994; Galy et al., Blood 85:2770–2778, 1995; Toki et al., Proc. Nat. Acad Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In *Culture of Hematopoietic Cells*. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddeli, R. A. In *Culture of Hematopoietic Cells*. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells*. R. I. Freshney, et al. eds. Vol *Culture of Hematopoietic Cells*. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshhey, et al. eds. Vol pp. 163–179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a career as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing*, pps. 71-112 (Maibach, H I and Rovee, D T, eds.), Year Book Medical Publishers, Inc., Chicago, as modified by Eaglstein and Menz, J. Invest. Dermatol 71:382-84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin α family, may be useful as a contraceptive based on the ability of inhibins to decrease fertility in female mammals and decrease spematogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562-572, 1972; Ling et al., Nature 321:779-782, 1986; Vale et al., Nature 321:776-779, 1986; Mason et al., Nature 318:659-663, 1985; Forage et al., Proc. Natl. Acad. Sci. USA 83:3091-3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744–1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell—cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in:Current Protocols in Immunology, Ed by J. E. Coligan, A. M. Kruisbeek, D. H. Margulies, E. M. Shevach, W.Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; StiTt et al., Cell 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell—cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Administration and Dosing

A protein of the present invention (from whatever source derived, including without limitation from recombinant and non-recombinant sources) may be used in a pharmaceutical composition when combined with a pharmaceutically acceptable career. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunolgobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 µg to about 100 mg (preferably about 0.1 µg to about 10 mg, more preferably about 0.1 µg to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

Patent and literature references cited herein are incorporated by reference as if fully set forth.

What is claimed is:

1. An isolated polynucleotide selected from the group consisting of:
    (a) a polynucleotide comprising the nucleotide sequence of SEQ ID NO:1;
    (b) a polynucleotide comprising the nucleotide sequence of SEQ ID NO:1 from nucleotide 218 to nucleotide 628;
    (c) a polynucleotide comprising the nucleotide sequence of the full length protein coding sequence of clone AJ26_3 deposited under accession number ATCC 98115;
    (d) a polynucleotide encoding the full length protein encoded by the cDNA insert of clone AJ26_3 deposited under accession number ATCC 98115;
    (e) a polynucleotide comprising the nucleotide sequence of the mature protein coding sequence of clone AJ26_3 deposited under accession number ATCC 98115;
    (f) a polynucleotide encoding the mature protein encoded by the cDNA insert of clone AJ26_3 deposited under accession number ATCC 98115;
    (g) a polynucleotide encoding a protein comprising the amino acid sequence of SEQ ID NO:2, said sequence of SEQ ID NO:2 being the sequence encoded by the cDNA insert of clone AJ26_3 deposited under accession number ATCC 98115;
    (h) a polynucleotide which is an allelic variant of a polynucleotide of (a)–(f) above; and
    (i) a polynucleotide capable of hybridizing under conditions of incubation at 65° C. in 6×SSC/0.5% SDS, followed by washing with 2×SSC/0.5% SDS at room temperature, with a polynucleotide consisting of the nucleotide sequence of SEQ ID NO:1 from nucleotide 218 to nucleotide 628.

2. An isolated polynucleotide of claim 1 wherein said polynucleotide is operably linked to an expression control sequence.

3. A host cell transformed with a polynucleotide of claim 2.

4. The host cell of claim 3, wherein said cell is a mammalian cell.

5. A process for producing a protein encoded by a polynucleotide of claim 2, which process comprises:
    (a) growing a culture of the host cell of claim 3 in a suitable culture medium; and
    (b) purifying said protein from the culture.

6. A protein produced according to the process of claim 5.

7. The protein of claim 6 comprising a mature protein.

8. An isolated protein, wherein said protein comprises an amino acid sequence selected from the group consisting of:

(a) the amino acid sequence of SEQ ID NO:2, said sequence of SEQ ID NO:2 being the sequence encoded by the cDNA insert of clone AJ26_3 deposited under accession number ATCC 98115;

(b) the amino acid sequence of SEQ ID NO:2 from amino acid 27 to amino acid 82; and (c) the amino acid sequence encoded by the cDNA insert of clone AJ26_3 deposited under accession number ATCC 98115;

the protein being substantially free from other mammalian proteins.

9. The protein of claim 8, wherein said protein comprises the amino acid sequence of SEQ ID NO:2, said sequence of SEQ ID NO:2 being the sequence encoded by the cDNA insert of clone AJ26_3 deposited under accession number ATCC. 98115.

10. The protein of claim 8, wherein said protein comprises the amino acid sequence of SEQ ID NO:2 from amino acid 27 to amino acid 82.

11. A composition comprising protein of claim 8, and a pharmaceutically acceptable carrier.

12. An isolated gene corresponding to the cDNA sequence of SEQ ID NO:1 and SEQ ID NO:3.

13. The polynucleotide of claim 1 wherein said polynucleotide comprises the nucleotide sequence of SEQ ID NO:1.

14. The polynucleotide of claim 1 wherein said polynucleotide comprises the nucleotide sequence of SEQ ID NO:1 from nucleotide 218 to nucleotide 628.

15. The polynucleotide of claim 1 wherein said polynucleotide comprises the nucleotide sequence of the full length protein coding sequence of clone AJ26_3 deposited under accession number ATCC 98115.

16. The polynucleotide of claim 1 wherein said polynucleotide comprises a polynucleotide encoding the full length protein encoded by the cDNA insert of clone AJ26_3 deposited under accession number ATCC 98115.

17. The polynucleotide of claim 1 wherein said polynucleotide comprises a polynucleotide comprising the nucleotide sequence of the mature protein coding sequence of clone AJ26_3 deposited under accession number ATCC 98115.

18. The polynucleotide of claim 1 wherein said polynucleotide comprises a polynucleotide encoding the mature protein encoded by the cDNA insert of clone AJ26_3 deposited under accession number ATCC 98115.

19. The polynucleotide of claim 1 wherein said polynucleotide comprises a polynucleotide encoding a protein comprising the amino acid sequence of SEQ ID NO:2, said sequence of SEQ ID NO:2 being the sequence encoded by the cDNA insert of clone AJ26_3 deposited under accession number ATCC 98115.

20. The polynucleotide of claim 1 wherein said polynucleotide comprises a polynucleotide capable of hybridizing under conditions of incubation at 65° C. in 6×SSC/0.5% SDS, followed by washing with 2×SSC/0.5% SDS at room temperature, with a polynucleotide consisting of the nucleotide sequence of SEQ ID NO:1 from nucleotide 218 to nucleotide 628.

21. The protein of claim 8 wherein said protein comprises the amino acid sequence encoded by the cDNA insert of clone AJ26_3 deposited under accession number ATCC 98115.

* * * * *

SEQUENCE LISTING ( 1 ) GENERAL INFORMATION:

( i i i ) NUMBER OF SEQUENCES: 71

( 2 ) INFORMATION FOR SEQ ID NO:1:

( i ) SEQUENCE CHARACTERISTICS:
( A ) LENGTH: 628 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| AAAAGAGGA | GGATTTGATA | TTCACNTGGC | CCGCGGNGAT | GCCTTTGAGG | GNGGCCGCGT | 60 |
| CCATNTGGTC | AGAAAAGACA | ATCTTTTTGT | TGTCAAGCTT | GAGGTGTGGC | AGGCTTGAGA | 120 |
| TCTGGCCATA | CACTTGAGTG | ACAATGACAT | CCANTTTGCC | TTTCTCTCCA | CAGGTGTCCA | 180 |
| NTCCCAGGTC | CAACTGCAGA | NTTCGAATTC | GGCCTTCATG | GCCTASGCAA | RCTACTGGCA | 240 |
| CCTGCTGYTC | TCAACTAACC | TCCACACAAT | GGTGTTCGCA | TTTTGGAAGG | TCTTTCTGAT | 300 |
| CCTAAGCTGC | CTTGCAGGTC | AGGTTAGTGT | GGTGCAAGTG | ACCATCCCAG | ACGGTTTCGT | 360 |
| GAACGTGACT | GTTGGATCTA | ATGTCACTCT | CATCTGCATC | TACACCACCA | CTGTGGCCTC | 420 |
| CCGAGAACAG | CTTTCCATCC | AGTGGTCTTT | CTTCCATAAG | AAGGAGATGG | AGCCAATTTC | 480 |
| TATTTACTTT | TCTCAAGGTG | GACAAGCTGT | AGCCATCGGG | CAATTTAAAG | ATCGAATTAC | 540 |
| AGGGTCCAAC | GATCCAGGTA | ATGCATCTAT | CACTATCTCG | CATATGCAGC | CAGCAGACAG | 600 |
| TGGAATTTAC | ATCTGCGATG | TTAACAAC | | | | 628 |

( 2 ) INFORMATION FOR SEQ ID NO:2:

( i ) SEQUENCE CHARACTERISTICS:
( A ) LENGTH: 137 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:2:

Met Ala Xaa Ala Xaa Tyr Trp His Leu Leu Xaa Ser Thr Asn Leu His
1               5                   10                  15

```
         Thr  Met  Val  Phe  Ala  Phe  Trp  Lys  Phe  Leu  Ile  Leu  Ser  Cys  Leu
                        20                  25                  30

Ala  Gly  Gln  Val  Ser  Val  Val  Gln  Val  Thr  Ile  Pro  Asp  Gly  Phe  Val
                        35                  40                  45

Asn  Val  Thr  Val  Gly  Ser  Asn  Val  Thr  Leu  Ile  Cys  Ile  Tyr  Thr  Thr
                        50                  55                  60

Thr  Val  Ala  Ser  Arg  Glu  Gln  Leu  Ser  Ile  Gln  Trp  Ser  Phe  Phe  His
         65                       70                  75                            80

Lys  Lys  Glu  Met  Glu  Pro  Ile  Ser  Ile  Tyr  Phe  Ser  Gln  Gly  Gly  Gln
                             85                       90                       95

Ala  Val  Ala  Ile  Gly  Gln  Phe  Lys  Asp  Arg  Ile  Thr  Gly  Ser  Asn  Asp
                        100                 105                 110

Pro  Gly  Asn  Ala  Ser  Ile  Thr  Ile  Ser  His  Met  Gln  Pro  Ala  Asp  Ser
                        115                 120                 125

Gly  Ile  Tyr  Ile  Cys  Asp  Val  Asn  Asn
                        130                 135
```

(2) INFORMATION FOR SEQ ID NO:3:

(i) SEQUENCE CHARACTERISTICS:
        (A) LENGTH: 358 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
ATGTTATCAC  NGTGTCNGAT  GTTATNNACT  TNGAAAGGCA  GTCCAGAAAA  GTGTTCTAAG    60
NGAANTCTTA  AGATCTATTT  TAGATAATTT  CAACTAATTA  AATAACCTGT  TTTACTGCCT   120
GNACATTCCA  CATTAATAAN  GNGATACCAA  TCTTATANGA  ATGCTAATAT  TACTAAAATG   180
CACTGATATC  ACTTNTTCTT  CCCCTGTNGA  AAAGCTTTCT  CATGATCATA  TTTCACCCAC   240
ATNTCACCTN  GAAGAAACTT  ACAGGTAGAC  TTACCTTTTC  ACTTGTGGAA  TTAATCATAT   300
TTAAATCTTA  CTTTAAGGCT  CAATAAATAA  TANTCATAAA  AAAAAAAAA   AAAAAAA     358
```

(2) INFORMATION FOR SEQ ID NO:4:

(i) SEQUENCE CHARACTERISTICS:
        (A) LENGTH: 271 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

```
TAATCATGCC  TCTTGGAAGT  NAGTTAACGG  GCGTGATTGT  GGAAAATGAA  AATATTACCA    60
AAGAAGGTGG  CTTATTGGAC  ATGGCCNNNA  AANAAAATGA  CTTNNATGCN  GAGCCCNNTT   120
TAAAGCAGAC  AATTAAAGCA  ACAGTNNAAA  ATGGCAANAA  NGATGGCNTT  GCTGTTGATC   180
NTGTTGTNGG  CCTGAATACN  GAAAATATG   CTGAAACTGT  CCAACTTNAN  CNTAAAAGAA   240
CCCCNGGTNA  AGTNAAAGAC  ATTTCCTTGA  A                                    271
```

(2) INFORMATION FOR SEQ ID NO:5:

(i) SEQUENCE CHARACTERISTICS:
        (A) LENGTH: 591 base pairs
        (B) TYPE: nucleic acid
        (C) STRANDEDNESS: double
        (D) TOPOLOGY: linear ( i i ) MOLECULE TYPE: cDNA ( x i ) SEQUENCE DESCRIPTION: SEQ ID NO:5:

| ATGGTNACAG | GTGCAGGTGT | TNTCCTGGGA | GATAATGATG | CACCACCAGG | AACAAGTGCC | 60 |
|---|---|---|---|---|---|---|
| AGCCAAGAAG | GAGATGGTTC | TGTGAATGAT | GGTACAGAAG | GTGAGAGTGC | AGTCACCAGC | 120 |
| ACGGGGATAA | CAGAAGATGG | AGAGGGGCCA | GCAAGTTGCA | CAGGTTCAGA | ANATTGCNTC | 180 |
| GAAGGCTTTG | CTATAAGTTC | TGAATCGGAA | GAAAATGGAG | AGAGTGCAAT | GGACAGCACA | 240 |
| GTGGCCAAAG | AAGGCACTAA | TGTACCATTA | GTTGCTGCTG | GTCCTTGTGA | TGATGAAGGC | 300 |
| ATTGTGACTA | GCACAGGCGC | NAAAGAGGAA | GACGAGGAAG | GGGAGGATGT | TGTGACTAGT | 360 |
| ACTGGAAGAG | GAAATGAAAT | TGGGCATGCT | TCAACTTGTA | CAGGGTTAGG | AGAAGAAAGT | 420 |
| GAAGGGGTCT | TGATTTGTGA | AAGTGCAGAA | GGGGACAGTC | AGATTGGTAC | TGTGGTAGAG | 480 |
| CATGTGGAAG | CTGAGGCTGG | AGCTGCCATC | ATGAATGCAA | ATGAAAATAA | TGTTGACAGC | 540 |
| ATGAGTGGCA | CAGAGAAAGG | AAGTAAAGAC | ACAGATATCT | GCTCCAGTGC | C | 591 |

( 2 ) INFORMATION FOR SEQ ID NO:6:

( i ) SEQUENCE CHARACTERISTICS:
( A ) LENGTH: 197 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:6:

```
Met Val Thr Gly Ala Gly Val Xaa Leu Gly Asp Asn Asp Ala Pro Pro
  1               5                  10                  15
Gly Thr Ser Ala Ser Gln Glu Gly Gly Ser Val Asn Asp Gly Thr
             20                  25                  30
Glu Gly Glu Ser Ala Val Thr Ser Thr Gly Ile Thr Glu Asp Gly Glu
             35                  40                  45
Gly Pro Ala Ser Cys Thr Gly Ser Glu Xaa Cys Xaa Glu Gly Phe Ala
     50                  55                  60
Ile Ser Ser Glu Ser Glu Glu Asn Gly Glu Ser Ala Met Asp Ser Thr
 65                  70                  75                  80
Val Ala Lys Glu Gly Thr Asn Val Pro Leu Val Ala Ala Gly Pro Cys
                 85                  90                  95
Asp Asp Glu Gly Ile Val Thr Ser Thr Gly Ala Lys Glu Glu Asp Glu
            100                 105                 110
Glu Gly Glu Asp Val Val Thr Ser Thr Gly Arg Gly Asn Glu Ile Gly
            115                 120                 125
His Ala Ser Thr Cys Thr Gly Leu Gly Glu Glu Ser Glu Gly Val Leu
    130                 135                 140
Ile Cys Glu Ser Ala Glu Gly Asp Ser Gln Ile Gly Thr Val Val Glu
145                 150                 155                 160
His Val Glu Ala Glu Ala Gly Ala Ala Ile Met Asn Ala Asn Glu Asn
                165                 170                 175
Asn Val Asp Ser Met Ser Gly Thr Glu Lys Gly Ser Lys Asp Thr Asp
            180                 185                 190
Ile Cys Ser Ser Ala
            195
```

( 2 ) INFORMATION FOR SEQ ID NO:7:

( i ) SEQUENCE CHARACTERISTICS:
   ( A ) LENGTH: 289 base pairs
   ( B ) TYPE: nucleic acid
   ( C ) STRANDEDNESS: double
   ( D ) TOPOLOGY: linear ( i i ) MOLECULE TYPE: cDNA ( x i ) SEQUENCE DESCRIPTION: SEQ ID NO:7:

| | | | | | |
|---|---|---|---|---|---|
| GTATGCCAAT | TTCCGCCAGC | ATTGACNGAC | ATGAAGAGAA | TCAGNTGACT | GCAGACAACC | 60 |
| CAGAAGGGAA | CGGTGACTTN | TCAGCCACAG | AAGTGAGCAA | GCACAAGTTC | CCCATGCCCA | 120 |
| GCTTAATTGC | TGAGAATAAC | TGTCGGTGTC | CTGGGCCAGT | CAGGGGAGGC | AAAGAACTGG | 180 |
| GTCCCGTGTT | GGCAGTGAGC | ACCGAGGAGG | GGCACAACGG | GCCATCAGTC | CACAAGCCNT | 240 |
| CTGCAGGGCA | AGGCCATCAA | GTGCTGTTTG | TGCGGAAAAA | AAAAAAAA | | 289 |

( 2 ) INFORMATION FOR SEQ ID NO:8:

( i ) SEQUENCE CHARACTERISTICS:
   ( A ) LENGTH: 429 base pairs
   ( B ) TYPE: nucleic acid
   ( C ) STRANDEDNESS: double
   ( D ) TOPOLOGY: linear ( i i ) MOLECULE TYPE: cDNA ( x i ) SEQUENCE DESCRIPTION: SEQ ID NO:8:

| | | | | | |
|---|---|---|---|---|---|
| CTTGGTCCAN | TTGGTTTNNT | TCGNTTCCCC | CTTTTTCTTC | CCCTTGGTTT | TCTTTTTTTT | 60 |
| CGGGCAACAA | TATTTTCCAA | GGCTAATACC | AAGGCANACC | AATTCAACTC | CCAAGGNTCG | 120 |
| GGAATTTTTA | ACCTTTTAAT | TNNATGGCCC | CTCCCACTCC | TTTTCTACGG | CGATTTGTCT | 180 |
| GTGTCTGGCC | CCCACCCACT | GCCCATCCCC | CATTGTTGTC | TGGATGTGGT | TCTATTTTTT | 240 |
| ATCGGTCTCC | TTTCCCCTCC | TCCCCGTTCT | CGCCCCCGCC | CCACCCCTG | CTCCCACTAC | 300 |
| CCTTTGTCTC | TTGCTCTTTC | TTGGGCTTCT | GTACAACTCA | ACTTGTATAC | ACTGTGTACA | 360 |
| CACAACCAGC | CAAACGAAAA | CCCAACGGCR | AAMAAAAAAA | AAAAAAAAAA | AAAAAAAAA | 420 |
| AAAAAAAA | | | | | | 429 |

( 2 ) INFORMATION FOR SEQ ID NO:9:

( i ) SEQUENCE CHARACTERISTICS:
   ( A ) LENGTH: 130 amino acids
   ( B ) TYPE: amino acid
   ( C ) STRANDEDNESS:
   ( D ) TOPOLOGY: linear ( i i ) MOLECULE TYPE: protein ( x i ) SEQUENCE DESCRIPTION: SEQ ID NO:9:

```
Leu Gly Pro Xaa Gly Xaa Xaa Arg Phe Pro Leu Phe Leu Pro Leu Gly
 1               5                  10                 15

Phe Leu Phe Phe Arg Ala Thr Ile Phe Ser Lys Ala Asn Thr Lys Ala
            20                  25                 30

Xaa Gln Phe Asn Ser Gln Gly Ser Gly Ile Phe Asn Leu Leu Ile Xaa
        35                  40                 45

Trp Pro Leu Pro Leu Leu Phe Tyr Gly Asp Leu Ser Val Ser Gly Pro
    50                  55                 60

His Pro Leu Pro Ile Pro His Cys Cys Leu Asp Val Val Leu Phe Phe
65                  70                  75                 80

Ile Gly Leu Leu Ser Pro Pro Arg Ser Arg Pro Arg Pro Thr Pro
            85                  90                 95
```

```
       Cys  Ser  His  Tyr  Pro  Leu  Ser  Leu  Ala  Leu  Ser  Trp  Ala  Ser  Val  Gln
                      100                      105                      110

Leu  Asn  Leu  Tyr  Thr  Leu  Cys  Thr  His  Asn  Gln  Pro  Asn  Glu  Asn  Pro
                      115                      120                      125

Thr  Ala
            130
```

( 2 ) INFORMATION FOR SEQ ID NO:10:

( i ) SEQUENCE CHARACTERISTICS:
        ( A ) LENGTH: 368 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:10:

```
TCTGTTCCCG  AACTGGAACT  GCGTTGGGAC  CCGTCGGATC  GTAAATCCCA  TGTNNGGTAT   60
CTGCCGTCGG  AAAATTTGAA  CTTTCTAATT  GGACACCTAA  CACCCACANT  CCTCCAGGTG  120
GGTCCTAAGG  ATCTTANGAA  CAACGATGGG  GGGTCCTAAN  CCAGGGGGGG  ATGAAGGTCT  180
GGCTCTCAAT  CCCCGCCTCG  CGGGGANTNC  CTCCCCCTC   TGCGATGGGG  GTCCTAAGAG  240
CCATTGGGGG  AACCAGGGGC  TGGCTCTCAA  TCCCTGCCTC  GCGGGGGGTG  CCTCCCCCCC  300
TGTGATGGGG  GTTCTAACAG  CCANGGGCGG  AANAAGGGAT  ATCTCTCACT  CCCCACCTTC  360
NCGGGGGG                                                                368
```

( 2 ) INFORMATION FOR SEQ ID NO:11:

( i ) SEQUENCE CHARACTERISTICS:
        ( A ) LENGTH: 396 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:11:

```
GAACTTTCTA  CTTGGACAAC  TAACACCCAC  AGTCCTCCAG  ACAGAAAGAC  AACAGGTACA   60
AAGCCCTAAG  GATTATAAAG  GTATGCTGCT  TACCATCATC  TTAGTGACCA  AGGCAGCGAA  120
GCTGTTTCTG  TACCTTGGAA  CAGTCTTCCC  TGACAAGCCA  GAGAACAGTG  ATAAAGCCAC  180
CAGCCTTGGG  ATCAGGACTG  AAAAGGCAAG  AGTGATGGAG  ATTTCTCCTG  CGCTAAGCCA  240
AGAGAAGGTT  TCAGCACTTC  AGACAGCTCC  CACCGAAGTA  GCCGCGTTCC  CAGCTGCTTG  300
CAGATGTTGA  AAAGGAAAGC  CTCGGTTTGT  CTTGAGGTTG  TCAGCAGGTG  CAAGACACGT  360
AATAAAATGC  AATGTGTTCC  TAAAAAAAAA  AAAAAA                              396
```

( 2 ) INFORMATION FOR SEQ ID NO:12:

( i ) SEQUENCE CHARACTERISTICS:
        ( A ) LENGTH: 75 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:12:

```
       Met  Leu  Leu  Thr  Ile  Ile  Leu  Val  Thr  Lys  Ala  Ala  Lys  Leu  Phe  Leu
       1                   5                        10                       15

Tyr  Leu  Gly  Thr  Val  Phe  Pro  Asp  Lys  Pro  Glu  Asn  Ser  Asp  Lys  Ala
```

```
                    20                      25                         30
    Thr  Ser  Leu  Gly  Ile  Arg  Thr  Glu  Lys  Ala  Arg  Val  Met  Glu  Ile  Ser
                   35                      40                         45

Pro  Ala  Leu  Ser  Gln  Glu  Lys  Val  Ser  Ala  Leu  Gln  Thr  Ala  Pro  Thr
         50                      55                         60

Glu  Val  Ala  Ala  Phe  Pro  Ala  Ala  Cys  Arg  Cys
    65                      70                      75
```

( 2 ) INFORMATION FOR SEQ ID NO:13:

( i ) SEQUENCE CHARACTERISTICS:
    ( A ) LENGTH: 429 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:13:

```
TCAGAAAAGA  CAATNTTTTA  GTAANAAAGN  ANTGAGGTGT  GGCAGGCTNG  AGATTTGGCC      60
ANANACTNGA  GTGACAANGA  CATCCACTTT  GCCTTTNTCT  CCACAGGTGT  CCACTCCCAG     120
GTCCAACTGC  AGATTTNGAA  TTCGGCNTTC  ATGGCCTAGC  CCCTTCCACC  TCTTCTCCTA     180
NGACTTGGAG  GANTCCTCCC  TGTCCACCAA  GGAGAAGGAA  GCAGANTCCC  AGAAGGAAAA     240
CAGANACAGC  AATTTTGGCA  ATAACTCTTA  TCACTCCTCA  AGACCCTCAT  CTGGATCCAG     300
TGTGCCCACC  ACCCCCACAT  CATCCGTCTC  ACCCCACAG   GAGGCCAGGT  TGGAAAGGTC     360
ATCACCGAGT  GGTCTTCTCA  CATCATCCTT  CAGGCAGCAC  CAAGAGTCAC  TGGCAAAAAA     420
AAAAAAAA                                                                  429
```

( 2 ) INFORMATION FOR SEQ ID NO:14:

( i ) SEQUENCE CHARACTERISTICS:
    ( A ) LENGTH: 138 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:14:

```
    Gln  Lys  Arg  Gln  Xaa  Phe  Ser  Xaa  Lys  Xaa  Xaa  Arg  Cys  Gly  Arg  Leu
    1                   5                   10                      15

Glu  Ile  Trp  Pro  Xaa  Thr  Xaa  Val  Thr  Xaa  Thr  Ser  Thr  Leu  Pro  Xaa
                        20                  25                      30

Ser  Pro  Gln  Val  Ser  Thr  Pro  Arg  Ser  Asn  Cys  Arg  Phe  Xaa  Ile  Arg
                   35                  40                       45

Xaa  Ser  Trp  Pro  Ser  Pro  Phe  His  Leu  Phe  Ser  Xaa  Asp  Leu  Glu  Xaa
         50                       55                       60

Ser  Ser  Leu  Ser  Thr  Lys  Glu  Lys  Glu  Ala  Xaa  Ser  Gln  Lys  Glu  Asn
    65                       70                       75                       80

Arg  Xaa  Ser  Asn  Phe  Gly  Asn  Asn  Ser  Tyr  His  Ser  Ser  Arg  Pro  Ser
                        85                       90                       95

Ser  Gly  Ser  Ser  Val  Pro  Thr  Thr  Pro  Thr  Ser  Ser  Val  Ser  Pro  Pro
                   100                      105                      110

Gln  Glu  Ala  Arg  Leu  Glu  Arg  Ser  Pro  Ser  Gly  Leu  Leu  Thr  Ser
                   115                      120                      125

Ser  Phe  Arg  Gln  His  Gln  Glu  Ser  Leu  Ala
                   130                      135
```

( 2 ) INFORMATION FOR SEQ ID NO:15:

( i ) SEQUENCE CHARACTERISTICS:
        ( A ) LENGTH: 218 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:15:

```
TGGCCTACCT GACCTCAGGT GATCTGCCCG CCTCGGCCTC TGAAAGTGCT GGGATTATAG      60

GCATGAGCCN ACATGCCTGA CCTGTTATTT ATTTTAAATT ATATCAGGAA TACACACACA     120

CACACACACA CACACACACA CACACACACA ACTTATAAAG ATAATGGTCT CCTTGGCACT     180

CCCACCCACC CACCCATCCA AATTTACACA AATTAATC                             218
```

( 2 ) INFORMATION FOR SEQ ID NO:16:

( i ) SEQUENCE CHARACTERISTICS:
        ( A ) LENGTH: 322 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:16:

```
ATCCAAATTN ACACAAGTAA ATCTGTAATC AATTTGGTTA GAAGGGATTT ATTTTAATAT      60

TTTTGGGGAT TGCTTAGATG CAGTATAATT TTTAGTTATA TTAGTAGTAA TTGGAAATGT     120

GTATTTTGT  GACTGAAGTC ACCTTCTAAA TAATTTCTAG AATAAAATTT TTATATTGAA     180

GAAGTTGGTN TTAACCATTT TTTTTCAGG  AGCATGCATT TTGAAATCAT TCTGTGGGAA     240

GATGAAAACA AATTTAGTTC TATGTCTCCC CTTTTAGAG  ATGTTGACAC TTTCCTTAAA     300

TGTACCATGC ATGATTTGTC TA                                              322
```

( 2 ) INFORMATION FOR SEQ ID NO:17:

( i ) SEQUENCE CHARACTERISTICS:
        ( A ) LENGTH: 27 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:17:

```
Met Lys Thr Asn Leu Val Leu Cys Leu Pro Phe Leu Glu Met Leu Thr
 1               5                  10                  15

Leu Ser Leu Asn Val Pro Cys Met Ile Cys Leu
                20              25
```

( 2 ) INFORMATION FOR SEQ ID NO:18:

( i ) SEQUENCE CHARACTERISTICS:
        ( A ) LENGTH: 379 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:18:

```
CAGTTTTGAT GTAAGTAAAT ACCCAACAGA AATGCAAACA TATACTTACC AAAACTCATG       60
```

TCCAAGAATA TTCGTAGAAG CACAATTCTT ATGATAGCAA AAAGGTAGAA AACAACTTAA    120

ATGTTTTTAA GCAGTAGCAT AAGAGTAATA CCGTGTGGTT TGTTTANACA GTGAGATCCT    180

GTACAGCCAT GTAAAGACC AAAATATTCC CTGTAACAAT GAGAATGAAT CTCCTGTGCT    240

TGCTTCGGCA GCACATACAN TAAAATTGGA ACGATACAGA GATTANCATG NCCCTGTGC    300

AAGGAGAATG AATTTTCGTA ATGTTCAGCA AAGAAGCCA GATATAAATG AATATTCCAT    360

TTTATAAAAA NAAAAAAA                                                 379

( 2 ) INFORMATION FOR SEQ ID NO:19:

( i ) SEQUENCE CHARACTERISTICS:
        ( A ) LENGTH: 456 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:19:

AAGAAGGAGA CTGTAAGCTT GTTTGTACAA AAACATACCA TACAGAGAAA GCTGAAGACA    60

AACAAAAGTT AGAATTCTTG AAAAAAAGCA TGTTATTGAA TTATCAACAT CACTGGATTG    120

TGGATAATAT GCCTGTAACG TGGTGTTACG ATGTTGAAGA TGGTCAGGTT CTGTAATCCT    180

GGATTTCCTA TTGGCTGTTA CATTACAGAT AAAGGCCATG CAAAAGATGC CTGTGTTATT    240

AGTTCAGATT TCCATGAAAG AGATACATTT TACATCTTCA ACCATGTTGA CATCAAAATA    300

TACTATCATG TTGTTGAAAC TGGGTCCATG GGAGCAAGAT TAGTGGCTGC TAAACTTGAA    360

CCGAAAAGCT TCAAACATAC CCATATAGAT AAACCAGACT GCTCAGGGCC CCCCATGGAC    420

ATAAGTAACA AGGCTTCTGG GGAGATAAAA ATTGCA                             456

( 2 ) INFORMATION FOR SEQ ID NO:20:

( i ) SEQUENCE CHARACTERISTICS:
        ( A ) LENGTH: 519 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:20:

CAANTAATAA ANCTTTTGTT TCCCTCGNCA TTGTNNTCGT TCCCCTGTCC NGCCTTGTTT    60

CCNNNGTCCT GCACCAATAT TTCCAAACCN AATACCCAAG CATACAATCC NNACTCCAAG    120

CTNGGAATTC GCCCANAGAG ACCGTCGNGG GAAGAANTTG NCTGGAAACT TGTTCATGGT    180

GATATATACC GTCCTCCAAG AAANGGGATG CTGCTATCAG TCTTTCTAGG AGCCGGGANA    240

CAGATATTAA TTATGACCTT TGTGACTCTA TTTTTCGCTT GCCTGGGAGT TTTGTCACCT    300

CCCANCCGAG GAGCGCTGAT GACGTGTGCT GTGGTCCTGT GGGTGCTGCT GGGCACCCCT    360

GCAGGCTATG TTTCTGCCAG ATTCTATAAG TCCTTTGGAG GTGAGAAGTG GAAAACAAAT    420

GTTTTATTAA CATCATTTCT TTGTCCTGGG ATTGTATTTG CTGACTTCTT TATAATGAAT    480

CTGATCCTCT GGTCAACGGC CTCTTTGGCC CTCGAGACA                          519

( 2 ) INFORMATION FOR SEQ ID NO:21:

( i ) SEQUENCE CHARACTERISTICS:
        ( A ) LENGTH: 89 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:21:

| Met | Thr | Phe | Val | Thr | Leu | Phe | Phe | Ala | Cys | Leu | Gly | Val | Leu | Ser | Pro |
| --- | --- | --- | --- | --- | --- | --- | --- | --- | --- | --- | --- | --- | --- | --- | --- |
| 1 | | | | 5 | | | | | 10 | | | | | 15 | |
| Pro | Xaa | Arg | Gly | Ala | Leu | Met | Thr | Cys | Ala | Val | Val | Leu | Trp | Val | Leu |
| | | | 20 | | | | | 25 | | | | | 30 | | |
| Leu | Gly | Thr | Pro | Ala | Gly | Tyr | Val | Ser | Ala | Arg | Phe | Tyr | Lys | Ser | Phe |
| | | 35 | | | | | 40 | | | | | 45 | | | |
| Gly | Gly | Glu | Lys | Trp | Lys | Thr | Asn | Val | Leu | Leu | Thr | Ser | Phe | Leu | Cys |
| | 50 | | | | | 55 | | | | | 60 | | | | |
| Pro | Gly | Ile | Val | Phe | Ala | Asp | Phe | Phe | Ile | Met | Asn | Leu | Ile | Leu | Trp |
| 65 | | | | | 70 | | | | | 75 | | | | | 80 |
| Ser | Thr | Ala | Ser | Leu | Ala | Leu | Glu | Thr | | | | | | | |
| | | | | 85 | | | | | | | | | | | |

( 2 ) INFORMATION FOR SEQ ID NO:22:

( i ) SEQUENCE CHARACTERISTICS:
( A ) LENGTH: 507 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:22:

```
TTCTTCCCAT ACACCTTTCC CCCATAAGAT GTGTCTTCAA CACTATAAAG CATTTGTATT      60
GTGATTTGAT TAAGTATATA TTTGGTTGTT CTCAATGAAG AGCAAATTTA AATATTATGT     120
GCATTTGTAA ATACAGTAGC TATAAAATTT TCCATACTTC TAATGGCAGA ATAGAGGAGG     180
CCATATTAAA TAATACTGAT GAAAGGCAGG ACACTGCATT GTAAATAGGA TTTTCTAGGC     240
TCGGTAGGCA GAAAGAATTA TTTTTCTTTG AAGGAAATAA CTTTTATCA TGGTAATTTT      300
GAAGGATGAT TCCTATGATG TGTTCACCAG GGGAATGTGG CTTTTAAAGA AAATCTTCTA     360
TTGGTTGTAA CTGTTCATAT CTTCTTACTT TTCTGTGTTG ACTTCATTAT TCCCATGGTA     420
TTGGCCTTTT AAACTATGTG CCTCTGAGTC TTTCAATTTA TAAATTTGTA TCTTAATAAA     480
TATTATAAAA ATGAAAAAAA AAAAAAA                                          507
```

( 2 ) INFORMATION FOR SEQ ID NO:23:

( i ) SEQUENCE CHARACTERISTICS:
( A ) LENGTH: 622 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:23:

```
GGTTCTTCGG GACACCCGTG GATGGACACG GNAAGGAAAC ACCAGGCCAA CCACAGNTGG      60
GGATANAATA GNACAACCAC ACCCTGCCGT CCAGAGCCTC CCAGNCTGTG CCCCGTCCTA     120
GTACCACCAG CAACCATCAA TCCCGTCTCC TCCTGCCTCC TCTCCTGCAA TCCACCCCGC     180
CACGACTATC GCCATGGCAG CCCTGATCGC AGAGAACTTC CGCTTCCTGT CACTTTTCTT     240
CAAGAGCAAG GATGTGATGA TTTTCAACGG CCTGGTGGCA CTGGGCACGG TGGGCAGCCA     300
GGAGCTGTTC TCTGTGGTGG CCTTCCACTG CCCCTGCTCG CCGGCCCGGA ACTACCTGTA     360
CGGGCTGGCG GCCATCGGCG TGCCCGCCCT GGTGCTCTTC ATCATTGGCA TCATCCTCAA     420
```

```
CAACCACACC  TGGAACCTCG  TGGCCGAGTG  CCAGCACCGG  AGGACCAAGA  ACTGCTCCGC      480

CGCCCCCACC  TTCCTCCTTC  TAAGCTCCAT  CCTGGGACGT  GCGGCTGTGG  CCCCTGTCAC      540

CTGGTCTGTC  ATCTCCCTGC  TGCGTGGTGA  GGCTTATGTC  TGTGCTCTCA  GTGAGTTCGT      600

GGACCCTTCC  TCACTCACGG  CC                                                  622
```

( 2 ) INFORMATION FOR SEQ ID NO:24:

( i ) SEQUENCE CHARACTERISTICS:
        ( A ) LENGTH: 143 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:24:

```
Met  Ala  Ala  Leu  Ile  Ala  Glu  Asn  Phe  Arg  Phe  Leu  Ser  Leu  Phe  Phe
 1              5                       10                      15

Lys  Ser  Lys  Asp  Val  Met  Ile  Phe  Asn  Gly  Leu  Val  Ala  Leu  Gly  Thr
               20                       25                      30

Val  Gly  Ser  Gln  Glu  Leu  Phe  Ser  Val  Val  Ala  Phe  His  Cys  Pro  Cys
          35                       40                      45

Ser  Pro  Ala  Arg  Asn  Tyr  Leu  Tyr  Gly  Leu  Ala  Ala  Ile  Gly  Val  Pro
     50                       55                      60

Ala  Leu  Val  Leu  Phe  Ile  Ile  Gly  Ile  Ile  Leu  Asn  Asn  His  Thr  Trp
65                       70                      75                       80

Asn  Leu  Val  Ala  Glu  Cys  Gln  His  Arg  Arg  Thr  Lys  Asn  Cys  Ser  Ala
                    85                       90                      95

Ala  Pro  Thr  Phe  Leu  Leu  Leu  Ser  Ser  Ile  Leu  Gly  Arg  Ala  Ala  Val
               100                      105                     110

Ala  Pro  Val  Thr  Trp  Ser  Val  Ile  Ser  Leu  Leu  Arg  Gly  Glu  Ala  Tyr
          115                      120                     125

Val  Cys  Ala  Leu  Ser  Glu  Phe  Val  Asp  Pro  Ser  Ser  Leu  Thr  Ala
     130                      135                     140
```

( 2 ) INFORMATION FOR SEQ ID NO:25:

( i ) SEQUENCE CHARACTERISTICS:
        ( A ) LENGTH: 314 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:25:

```
TTTTAAAAAA  CTTTTATCTT  CTTGGCCAGG  GGAAAGGNCC  CCCAGGCAAN  CTGGGGTNTG       60

GANANACCCA  NAAAACNATG  GNANCCCCAA  CCANCAGGGC  CAGGTTACAG  TGNAACTCCC      120

CAGTGGGCCC  CNTTATGGGA  CTCNATTCAG  TTAANATTTA  TCTANCTTCA  NAGGGACACC      180

CANCCCAACA  GTTCCCCNCT  GGGGAGTGGC  CCCCANTTCA  ACCTCTGGCC  TTANTTTAAA      240

AAATTAAANT  TTTNANAAAG  TTTTCTTAC   TAAAAGGGAA  AAAAAAAAAA  AAAAAAAAA       300

AAAAAAAAAA  AAAA                                                           314
```

( 2 ) INFORMATION FOR SEQ ID NO:26:

( i ) SEQUENCE CHARACTERISTICS:
        ( A ) LENGTH: 533 base pairs
        ( B ) TYPE: nucleic acid ( C ) STRANDEDNESS: double
( D ) TOPOLOGY: linear ( i i ) MOLECULE TYPE: cDNA ( x i ) SEQUENCE DESCRIPTION: SEQ ID NO:26:

| | | | | | |
|---|---|---|---|---|---|
| GGGATATCCC | ATACAGGTAT | GAAAAAACCC | CNTATGTNAT | AGTGTTCTAT | AGCACACAAT 60 |
| ACCTTATGAA | GGAAGGGTTT | SATGAATACA | TGGCAGAAGA | CAATCATGAA | AGAMTTATYT 120 |
| TGAGGGGYTA | GAARTAATGA | GTTTGGAGGT | GTGCCCCTTA | GGTCCTGART | GTCCTGGGAT 180 |
| CCCTMACCCC | TAATTTCTCT | CCCARAGCAT | YATCCCTTCT | CAGTATTGGT | ACTACATGAT 240 |
| TGAACTTTCC | TTCTASTGGT | CCCTGYTCTT | CAGCATTGCC | TCTGATGTCW | AGCGAAAGGA 300 |
| TTTTAAGGAA | CAGATCATCC | ACCATGTGGC | CACTATCATT | CTCCTCTGCT | TCTCCTGGTT 360 |
| TGCCAATTAC | GTCCGGGCAG | GGACCCTCAT | CATGGCTCTG | CATGACGCTT | CTGACTACCT 420 |
| GCTGGAGTCT | GCCAAGATGT | TAACTACGC | GGGATGGAAG | AACACCTGCA | ACAACCTCTT 480 |
| CATTGTGTTC | GCCATCGTTT | TCATCATCAC | TCGGCTGGTT | ATCATGCCTT | TCT 533 |

( 2 ) INFORMATION FOR SEQ ID NO:27:

( i ) SEQUENCE CHARACTERISTICS:
( A ) LENGTH: 44 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:27:

Met Thr Leu Leu Thr Thr Cys Trp Ser Leu Pro Arg Cys Leu Thr Thr
1               5                   10                  15

Arg Asp Gly Arg Thr Pro Ala Thr Thr Ser Ser Leu Cys Ser Pro Ser
            20                  25                  30

Phe Ser Ser Ser Leu Gly Trp Leu Ser Cys Leu Ser
        35                  40

( 2 ) INFORMATION FOR SEQ ID NO:28:

( i ) SEQUENCE CHARACTERISTICS:
( A ) LENGTH: 313 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:28:

| | | | | | |
|---|---|---|---|---|---|
| AAANACAAGT | CAATGAAGTG | AAGGAGGGTA | TGNANACATG | CCCCTCACCA | TACCCCAGGG 60 |
| ACCATGGTTC | CTAGGATCTC | ACTGCCTCCC | TTTNTGGCCT | TCCTGTCCCC | TCCCTTCAGC 120 |
| TATGACAGCT | GGTGTGGAGT | AGAAGGGCAA | CTAGTTCTGT | TATTTATTGA | ACATTTGGGG 180 |
| TTTCAGTTGT | AAAGCCACAA | CTACAGGTAG | GACCTGATAT | TTCGGNGAGG | GACCATTTCA 240 |
| GACCAAAATG | TACTGTTAAT | TTTTTTTAAT | TAAAGTATAT | TAAAGGTTAA | ATAAAAAAA 300 |
| AAAAAAAAAA | AAA | | | | 313 |

( 2 ) INFORMATION FOR SEQ ID NO:29:

( i ) SEQUENCE CHARACTERISTICS:
( A ) LENGTH: 525 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:29:

| AAAGACATCC | ACTTTGCCTT | TNTCTCCACA | GGTGTCCACT | CCCAGGTCCA | ANTGNAGGNG | 60 |
| AGCCTGAATT | CGGCCAAAGA | GGCCTAATTA | CAATCATTTC | AAATTTTGAA | TTTTTAAGTT | 120 |
| GATGGGCTCT | TAAGTGGTCC | GTTCTGAATA | RAAACCAATT | TGCTAGTTTC | GGTTTTGTTT | 180 |
| TGTTTTGTTT | TGTTTTGTTT | TGTTTTGTTT | TTTAAGGAA  | TCAGATAGCC | AGAAAAAAAA | 240 |
| ATGCTATTGC | TTGTTTTCAT | GAACTTCAGT | TGTCTCTTTT | TAGTAAACCC | AGTACTTTCC | 300 |
| ACAAAGTCTT | CTCTGACCTT | CCCCATCACT | GGACGGTTCA | CCCATCTTCT | TCTCCAAGTG | 360 |
| TTTATCCCCC | AGCCCAAGCC | TTTCCTGCTG | CAAGCCAAGC | CTGCTACATT | TGTTACAGAC | 420 |
| CAAGCTTATA | CACAGCTCGA | CAACTGCACT | CCCACTGTAG | GCTCCGGTGT | GTACTCTTGT | 480 |
| CTTGTGTTGG | GAAGGGGAAG | TGAAGTGATA | AGCCAGAATT | TTTTT      |            | 525 |

( 2 ) INFORMATION FOR SEQ ID NO:30:

( i ) SEQUENCE CHARACTERISTICS:
  ( A ) LENGTH: 95 amino acids
  ( B ) TYPE: amino acid
  ( C ) STRANDEDNESS:
  ( D ) TOPOLOGY: linear ( i i ) MOLECULE TYPE: protein ( x i ) SEQUENCE DESCRIPTION: SEQ ID NO:30:

```
Met Leu Leu Leu Val Phe Met Asn Phe Ser Cys Leu Phe Leu Val Asn
 1               5                  10                  15
Pro Val Leu Ser Thr Lys Ser Ser Leu Thr Phe Pro Ile Thr Gly Arg
             20                  25                  30
Phe Thr His Leu Leu Leu Gln Val Phe Ile Pro Gln Pro Lys Pro Phe
         35                  40                  45
Leu Leu Gln Ala Lys Pro Ala Thr Phe Val Thr Asp Gln Ala Tyr Thr
     50                  55                  60
Gln Leu Asp Asn Cys Thr Pro Thr Val Gly Ser Gly Val Tyr Ser Cys
 65                  70                  75                  80
Leu Val Leu Gly Arg Gly Ser Glu Val Ile Ser Gln Asn Phe Phe
                 85                  90                  95
```

( 2 ) INFORMATION FOR SEQ ID NO:31:

( i ) SEQUENCE CHARACTERISTICS:
  ( A ) LENGTH: 270 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:31:

| AGGTTTCTTG | GGAACAGCTC | AGCAGATTTT | TGAGACCAAT | CAAATGNCCT | CATTAAGAAC | 60 |
| TTTATCTGTT | NGGAAACATG | GCTTCCTTCC | NGGNTCTGCT | AAACNGAAAG | CTCATTTGTT | 120 |
| GTTGCTGTTG | TTGTTGTTTG | TTTGTCCATT | TCTCTTTAAT | TCTAATGTTN | ACATCATGTC | 180 |
| GTGCTGTANG | ANTCTAGAAA | GCCTTAATTN | ACTTCCACCA | AGAAATAAAG | CAATATGTTG | 240 |
| GTAATNNGAA | AAAAAAAAA  | AAAAAAAAA  |            |            |            | 270 |

( 2 ) INFORMATION FOR SEQ ID NO:32:

( i ) SEQUENCE CHARACTERISTICS:
   ( A ) LENGTH: 574 base pairs
   ( B ) TYPE: nucleic acid
   ( C ) STRANDEDNESS: double
   ( D ) TOPOLOGY: linear ( i i ) MOLECULE TYPE: cDNA ( x i ) SEQUENCE DESCRIPTION: SEQ ID NO:32:

| | | | | | |
|---|---|---|---|---|---|
| TTTGGTCANA | AAAGACAATT | TTTTGTTNT | CAAGCTNGAG | GTGTGGCAGG | CTNGANATTT | 60 |
| GGCCAAANAA | TNGAGGGACA | AAGANATCCA | CTTTGCCTTT | TTTTCCACAG | GTGTCCANTC | 120 |
| CCAGGTCCAA | NTGCAGGCGG | GTCCACAGGC | CGCAGCCATG | GGTAGCCGNN | TNTCCCGAGN | 180 |
| GGARTTCGAA | TGGGTYTACA | CGGACCARCC | CCACGCCGCC | CGGCGCAAGG | AGATCTTAGC | 240 |
| AAAGTATCCA | GANATCAAGT | CCTTGATGAA | ACCTGACCAC | AATCTGATCT | GGATTGTAGC | 300 |
| CATGATGCTT | CTCGTCCAGC | TGGCTTCATT | TTACTTAGTC | AAAGATTTGG | ACTGGAAATG | 360 |
| GGTCATATTT | TGGTCCTATG | TCTTTGGCAG | CTGCCTTAAC | CACTCCATGA | CTCTGGCTAT | 420 |
| CCATGAGATT | TCCCACAATT | TCCCCTTNGG | CNCCNCNANG | GCCTGTGGAA | CCGCNGGTTT | 480 |
| GGAATGTTTG | CTAACCTCTC | TCTCCGAATG | GCCTACTCCA | TTTCCTTTAA | AAAAAACACA | 540 |
| TGGATCACCN | CCGGTACTCC | GAACGGATAA | ANTR | | | 574 |

( 2 ) INFORMATION FOR SEQ ID NO:33:

( i ) SEQUENCE CHARACTERISTICS:
   ( A ) LENGTH: 138 amino acids
   ( B ) TYPE: amino acid
   ( C ) STRANDEDNESS:
   ( D ) TOPOLOGY: linear ( i i ) MOLECULE TYPE: protein ( x i ) SEQUENCE DESCRIPTION: SEQ ID NO:33:

| Met | Gly | Ser | Arg | Xaa | Ser | Arg | Xaa | Glu | Phe | Glu | Trp | Val | Tyr | Thr | Asp |
|---|---|---|---|---|---|---|---|---|---|---|---|---|---|---|---|
| 1 | | | | 5 | | | | | 10 | | | | | 15 | |
| Gln | Pro | His | Ala | Ala | Arg | Arg | Lys | Glu | Ile | Leu | Ala | Lys | Tyr | Pro | Xaa |
| | | | 20 | | | | 25 | | | | | 30 | | | |
| Ile | Lys | Ser | Leu | Met | Lys | Pro | Asp | His | Asn | Leu | Ile | Trp | Ile | Val | Ala |
| | | 35 | | | | | 40 | | | | | 45 | | | |
| Met | Met | Leu | Leu | Val | Gln | Leu | Ala | Ser | Phe | Tyr | Leu | Val | Lys | Asp | Leu |
| | 50 | | | | | 55 | | | | | 60 | | | | |
| Asp | Trp | Lys | Trp | Val | Ile | Phe | Trp | Ser | Tyr | Val | Phe | Gly | Ser | Cys | Leu |
| 65 | | | | | 70 | | | | | 75 | | | | | 80 |
| Asn | His | Ser | Met | Thr | Leu | Ala | Ile | His | Glu | Ile | Ser | His | Asn | Phe | Pro |
| | | | | 85 | | | | | 90 | | | | | 95 | |
| Xaa | Gly | Xaa | Xaa | Xaa | Ala | Cys | Gly | Thr | Ala | Gly | Leu | Glu | Cys | Leu | Leu |
| | | | 100 | | | | | 105 | | | | | 110 | | |
| Thr | Ser | Leu | Ser | Glu | Trp | Pro | Thr | Pro | Phe | Pro | Leu | Lys | Lys | Thr | His |
| | | 115 | | | | | 120 | | | | | 125 | | | |
| Gly | Ser | Pro | Pro | Val | Leu | Arg | Thr | Asp | Lys | | | | | | |
| | 130 | | | | | 135 | | | | | | | | | |

( 2 ) INFORMATION FOR SEQ ID NO:34:

( i ) SEQUENCE CHARACTERISTICS:
   ( A ) LENGTH: 216 base pairs
   ( B ) TYPE: nucleic acid
   ( C ) STRANDEDNESS: double
   ( D ) TOPOLOGY: linear ( i i ) MOLECULE TYPE: cDNA ( x i ) SEQUENCE DESCRIPTION: SEQ ID NO:34:

| | | | | | |
|---|---|---|---|---|---|
| ATGAAGTGCT | TTTTGGAGGA | GCTTTTGTTT | AGTCCAACAG | GAGTCCAAGG | ATGCAGATTA | 60 |
| GAGTTTTGNG | AGTTTGCTGC | CCTTGNTGGG | CTAGGCATTT | CATTGTTGTA | ACTNCNTCNG | 120 |
| AGTAACTGAT | GATCCTATAA | GNAACCCCAA | TAAATTTTTT | GGTTACTAA | AAAAAAAAAA | 180 |
| AAAAAAAAA | AAAAAAAAA | AAAAAAAAA | AAAAA | | | 216 |

( 2 ) INFORMATION FOR SEQ ID NO:35:

( i ) SEQUENCE CHARACTERISTICS:
        ( A ) LENGTH: 526 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:35:

| | | | | | |
|---|---|---|---|---|---|
| ACAGGNGTCC | AATCCCAGGT | CCAANTGCAG | GGGAGCCTGA | ATTCGGCCAA | AGNGGCCTAG | 60 |
| CCTCCCAAGT | GSTGGGATTA | AAGGSGTGTG | CCACCATGCC | CCACTTCATA | TGTTATATTT | 120 |
| TTAATGAATA | AAGAGTGGAA | AAATTATGTA | TCACATGTGT | TAATTTGGGG | AGAAGCGCTT | 180 |
| TATAACAGAG | GGCTTACTYT | CAATTAAAGA | GAACAAAGGR | AAATGTGTTY | TACAGGCAGT | 240 |
| GTATACCTTT | GACCTCTGAA | AAAACCTATA | TAGTTTCTCC | TACAGACACC | TTGCCAGTAA | 300 |
| CCTTACAGGT | CTTATAGGAG | AGCAGATCCA | AGTTGCCAGG | CTGATCTGCA | AGCACAAACA | 360 |
| TTTGTCAAGG | GAAAGCACAG | GTCGTTACTT | TCAGTACAAA | ATGGTTCTTT | GCTATGGATG | 420 |
| GATTCTCTTC | TTCTTGCCCC | ATGTCCTGTT | CCCAAGGACC | GACTTCCTGC | AGCACTGTGG | 480 |
| TGGACTCTTC | TATGAGGAGA | CAACATCTGG | GCCTTATTCA | ATAGCC | | 526 |

( 2 ) INFORMATION FOR SEQ ID NO:36:

( i ) SEQUENCE CHARACTERISTICS:
        ( A ) LENGTH: 42 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:36:

| Met | Val | Leu | Cys | Tyr | Gly | Trp | Ile | Leu | Phe | Phe | Leu | Pro | His | Val | Leu |
|---|---|---|---|---|---|---|---|---|---|---|---|---|---|---|---|
| 1 | | | | 5 | | | | | 10 | | | | | 15 | |
| Phe | Pro | Arg | Thr | Asp | Phe | Leu | Gln | His | Cys | Gly | Gly | Leu | Phe | Tyr | Glu |
| | | | 20 | | | | | 25 | | | | | 30 | | |
| Glu | Thr | Thr | Ser | Gly | Pro | Tyr | Ser | Ile | Ala | | | | | | |
| | | 35 | | | | | 40 | | | | | | | | |

( 2 ) INFORMATION FOR SEQ ID NO:37:

( i ) SEQUENCE CHARACTERISTICS:
        ( A ) LENGTH: 208 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:37:

| | | | | | |
|---|---|---|---|---|---|
| TTTGAAANGG | CAACAGAAAT | ATTTTTTGNA | NTAGAAAAAG | GNATGGAACG | TGGTNCCAAT | 60 |
| TGTTNATTTT | CCTTNATTTA | TTCCCNGTAA | NTTTGTCNGN | NGATAAATTG | AANATAACNG | 120 |

5,708,157

73                                                                                      74

-continued

NGATTAANGN NTNATGNTAA AAAAAAAAAA AAAAAAAAA NAAAAAAAAA AAAAAAAAA          180

AAAAAAAAAA AAAAAAAAAA AAAAAAA                                                       208

( 2 ) INFORMATION FOR SEQ ID NO:38:

( i ) SEQUENCE CHARACTERISTICS:
      ( A ) LENGTH: 535 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:38:

ATTTGNTCAG AAAAGACAAT TTTTTTGTTN TCAAGCTTGA GGTGTGGCAG GCTTGAGATN          60

TGCCCANACA CTTGAGGGAC AANGACATCC AATAACCCNT TCTCTCCACA GGTGNCCACT         120

CCCAGGTCCA ACTGCAGGCG AGCCNGAATT CGGCCAAAGN GGCCAAGAT CAGTTAGCTC          180

CCTGGGTCGG AACAAGGTGA AAAGCAGCTT TCTTGCTTTT GAAATCATYT TTGTGACAAG         240

GACACATGGG GTCAGGGTAG GGTGTCCART TAAAATAGTG TCACTGCTTA GAAAGGGGWA         300

CTTGGATTCC TTTAGTTAGC TTAGCTCTGT CTCTTGTTTC ATAAAACACA CTGGGTTAGA         360

ATARAGGCTC CTGCATTACA TGGTTTGTGT CACTGTTTTT TGTTGGGTTT TCTTTTTGGT         420

TTTTCGAGAC AGGGTTTCTC TGTATAGCCC TGGCTGTCCT ARAACTCACT CTGTAGACCA         480

GGCTGGCCTC GAACTCAGAA ATCTGCCCGC TTCTGCCTCC CAAGTGCTGG GATTA             535

( 2 ) INFORMATION FOR SEQ ID NO:39:

( i ) SEQUENCE CHARACTERISTICS:
      ( A ) LENGTH: 52 amino acids
      ( B ) TYPE: amino acid
      ( C ) STRANDEDNESS:
      ( D ) TOPOLOGY: linear ( i i ) MOLECULE TYPE: protein ( x i ) SEQUENCE DESCRIPTION: SEQ ID NO:39:

Met Val Cys Val Thr Val Phe Cys Trp Val Phe Phe Leu Val Phe Arg
1               5                   10                  15

Asp Arg Val Ser Leu Tyr Ser Pro Gly Cys Pro Xaa Thr His Ser Val
                20                  25                  30

Asp Gln Ala Gly Leu Glu Leu Arg Asn Leu Pro Ala Ser Ala Ser Gln
            35                  40                  45

Val Leu Gly Leu
        50

( 2 ) INFORMATION FOR SEQ ID NO:40:

( i ) SEQUENCE CHARACTERISTICS:
      ( A ) LENGTH: 308 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:40:

GGATTAAAGG CATGTGTCAC GTTTTAAATT GATAGTTATA ACNTCGATGC CACGAATCCT          60

GCAGTTTCTC CTGTGCTCCT TTCTTTGTGT CAGATGGGTT AAGGGTTATC AGTTNGGGA          120

AGAATTGTCC TTGNACCCCC TGGAATTATT TTTCTCAAAA ATCCAAGACT CCAAAGAACA         180

```
TGGGAAAAAT TGTTCTGTCC ACTTTTGACG TTGAAGATTT TGGTTATCCT TTTCGTACTT      240

TCTATGTATT TTCTATGTAA AATTTTACAC AATTAAAAAT GTTTTTTGT  CTAGTAAAAA      300

AAAAAAAA                                                               308
```

(2) INFORMATION FOR SEQ ID NO:41:

(i) SEQUENCE CHARACTERISTICS:
        (A) LENGTH: 520 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:41:

```
CAGCNCGCGG ANCCGGCGTC CCGTTGGCGC GCTCTGGYMT GGMWTCGNGG TMGTCGNYTT      60

CGGCCCCGAR GAGCCGCTCG CTGTYTCCSG AGCGGCGGAR ARGATGSTGC GGGGCAGCCS     120

GGGGCCCGCY GCGCGCCGCC GSGAGTGAAC AGGGCCAGGC CGCGGGCGTC CGCKGGCTCG     180

AACCSCCAGT YTGCAGGGGC GKTTGCCGST GGTGGGAAAC ATGTTCAGTA TCAACCCCCT     240

GGAGAACCTG AAGCTGTACA TCAGCAGCCG GCCGCCCTTG GTGGTTTTA  TGATCAGTGT     300

CAGCGCCATG GCCATCGCCT TCCTCACCCT GGGCTACTTC TTCAAGATCA AGGAGATTAA     360

GTCCCCAGAA ATGGCTGAGG ATTGGAATAC TTTTCTGCTC CGGTTTAATG ATTTGGACTT     420

GTGTGTATCA GAAAACGAGA CACTGAAGCA TCTCTCCAAC GATACCACCA CACCAGAGAG     480

CACCATGACC GTCGGGCAGG CCAGATCGTC TACCCAGCCG                           520
```

(2) INFORMATION FOR SEQ ID NO:42:

(i) SEQUENCE CHARACTERISTICS:
        (A) LENGTH: 100 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:42:

```
Met Phe Ser Ile Asn Pro Leu Glu Asn Leu Lys Leu Tyr Ile Ser Ser
 1               5                  10                  15

Arg Pro Pro Leu Val Val Phe Met Ile Ser Val Ser Ala Met Ala Ile
                20                  25                  30

Ala Phe Leu Thr Leu Gly Tyr Phe Phe Lys Ile Lys Glu Ile Lys Ser
                35                  40                  45

Pro Glu Met Ala Glu Asp Trp Asn Thr Phe Leu Leu Arg Phe Asn Asp
    50                  55                  60

Leu Asp Leu Cys Val Ser Glu Asn Glu Thr Leu Lys His Leu Ser Asn
 65                  70                  75                  80

Asp Thr Thr Thr Pro Glu Ser Thr Met Thr Val Gly Gln Ala Arg Ser
                85                  90                  95

Ser Thr Gln Pro
            100
```

(2) INFORMATION FOR SEQ ID NO:43:

(i) SEQUENCE CHARACTERISTICS:
        (A) LENGTH: 244 base pairs
        (B) TYPE: nucleic acid
        (C) STRANDEDNESS: double
        (D) TOPOLOGY: linear ( i i ) MOLECULE TYPE: cDNA ( x i ) SEQUENCE DESCRIPTION: SEQ ID NO:43:

| | | | | | |
|---|---|---|---|---|---|
| GCGGCAGAGC | AATCCTGAAT | TTTGCCANGA | GAAGGNGGTT | NTGGCTGACG | CCTAATCNNA | 60 |
| CAGCTCCCCA | TTTTTTGAGA | GACCAAGAAC | CATGATCATT | GCCTGCTGAA | TCGGCCAGGG | 120 |
| CCTGGCCANT | CTGTGAANAC | ATGATCTTGC | AATGTTGGGT | TATTCCAGCC | AAAGACATTT | 180 |
| CAAGTGCCTG | TAANTGATTT | GTCCATATTT | ATAAACACTG | ATNTGGNAAA | AAAAAAAAA | 240 |
| AAAA | | | | | | 244 |

( 2 ) INFORMATION FOR SEQ ID NO:44:

( i ) SEQUENCE CHARACTERISTICS:
        ( A ) LENGTH: 848 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:44:

| | | | | | |
|---|---|---|---|---|---|
| AGCTGTTGGG | NTCGCGGTTG | AGGACAAATN | TTCGCGGTCT | TTCCAGTATT | CTTGGATCGG | 60 |
| AAACCCGTCG | GCTTCCGAAC | GGTACTCCGC | CACCGAGGGA | CCTGAGCGAG | TCCGCATCGA | 120 |
| CCGGATCGGA | AAACCTNTCG | ACTGTTGGGG | TGAGTACTCC | CTCTCAAAAG | CGGGCATGAC | 180 |
| TTNTGCGCTA | AGATTGTCAG | TTTCCAAAAA | CGAGGAGGAT | TTGATATTCA | CCTGGCCCGC | 240 |
| GGTGATGCCT | TTGAGGGTGG | CCGCGTCCAT | CTGGTCAGAA | AAGACAATCT | TTTTGTTGTC | 300 |
| AAGCTTGAGG | TGTGGCAGGC | TTGAGATCTG | GCCATACACT | TGAGTGACAA | TGACATCCAC | 360 |
| TTTGCCTTTN | TCTCCACAGG | TGTCCACTCC | CAGGTCCAAC | TGCAGACTTC | GAATTCGGCC | 420 |
| AAAGAGGCCT | ACTTTCATAT | CCACGATGCG | TTTTCTGGCC | GCCACGATCC | TGCTGCTGGC | 480 |
| GCTGGTCGCT | GCCAGCCAGG | CGGAGCCCCT | GCACTTCAAG | GACTGCGGCT | CTAAGGTGGG | 540 |
| AGTTATAAAG | GAGGTGAATG | TGAGCCCATG | TCCCACCGAT | CCCTGTCAGC | TGCACAAAGG | 600 |
| CCAGTCCTAC | AGTGTCAACA | TCACCTTTAC | CAGCGGCACT | CAGTCCCANA | ACAGCACGGC | 660 |
| CTTGGTCCAC | GGCATCCTGG | AAGGGATCCG | GGTCCCCTTC | CCTATTCCTG | ANCCTGACGG | 720 |
| TTGTNANANT | GGAATCAACT | GCCCCNTCCA | GAAAGACAAN | GTCTACAGCT | ACCTGAATAA | 780 |
| GCTTCCGGTG | AAAAATGAAT | ACCCCTCTAT | AAAACTGGTG | GTGGAATGGA | AACTTTGAAN | 840 |
| ATGACAAA | | | | | | 848 |

( 2 ) INFORMATION FOR SEQ ID NO:45:

( i ) SEQUENCE CHARACTERISTICS:
        ( A ) LENGTH: 130 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:45:

| Met | Arg | Phe | Leu | Ala | Ala | Thr | Ile | Leu | Leu | Leu | Ala | Leu | Val | Ala | Ala |
|---|---|---|---|---|---|---|---|---|---|---|---|---|---|---|---|
| 1 | | | | 5 | | | | | 10 | | | | | 15 | |
| Ser | Gln | Ala | Glu | Pro | Leu | His | Phe | Lys | Asp | Cys | Gly | Ser | Lys | Val | Gly |
| | | | 20 | | | | | 25 | | | | | 30 | | |
| Val | Ile | Lys | Glu | Val | Asn | Val | Ser | Pro | Cys | Pro | Thr | Asp | Pro | Cys | Gln |
| | | | 35 | | | | | 40 | | | | | 45 | | |
| Leu | His | Lys | Gly | Gln | Ser | Tyr | Ser | Val | Asn | Ile | Thr | Phe | Thr | Ser | Gly |

```
              50                       55                       60
    Thr  Gln  Ser  Xaa  Asn  Ser  Thr  Ala  Leu  Val  His  Gly  Ile  Leu  Glu  Gly
    65                       70                       75                       80

Ile  Arg  Val  Pro  Phe  Pro  Ile  Pro  Xaa  Pro  Asp  Gly  Cys  Xaa  Xaa  Gly
                        85                       90                       95

Ile  Asn  Cys  Pro  Xaa  Gln  Lys  Asp  Xaa  Val  Tyr  Ser  Tyr  Leu  Asn  Lys
                   100                      105                      110

Leu  Pro  Val  Lys  Asn  Glu  Tyr  Pro  Ser  Ile  Lys  Leu  Val  Val  Glu  Trp
              115                      120                      125

Lys  Leu
         130
```

( 2 ) INFORMATION FOR SEQ ID NO:46:

( i ) SEQUENCE CHARACTERISTICS:
        ( A ) LENGTH: 265 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:46:

```
GNGTTACCTC  CCCTGTTTCT  AAGTGCCTCC  TGAGTCCCCA  GCCCCTGGCT  TATCAGTCAG    60
ATGAGTNTCC  TTGGNAGCNT  CTGCCCCATC  GCTTCAGCAG  NAGNGACTAG  NTTTCCTCGG   120
NATCCAGACT  GGNTGNGGGG  CAGTCTGCCG  CAGAAANTTG  TNTNTGAGTG  GNTGNGTCTT   180
TGNGGTNAGC  TNTCGTTCNN  TGGTAGTNTT  NATTAAAGCC  AANANTNGGT  TGCAAAAAAA   240
AANNGNAAAA  AAAAAAAAA   AAAAA                                            265
```

( 2 ) INFORMATION FOR SEQ ID NO:47:

( i ) SEQUENCE CHARACTERISTICS:
        ( A ) LENGTH: 374 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:47:

```
GCGGCCGCAG  GTCTANAATT  CAATCGGGCT  GCCTTATCGC  CAAGCTCCTT  CAGGAGAACA    60
AAGAACAGGC  CATTACCCTG  GAAAANACTG  GCAACTGATT  TTACCCACAA  GCCCNAACCT   120
CAGGGATTTC  AGTATCTACT  ANTCTGGGTN  NATACTTTCA  CGGGTTGGGC  AGAAGCCTTC   180
CCCTGTTGGA  CAGAAAANGC  CCNAGANGTT  NTAAAGGCAC  TAGTTCATGA  AATAATTCCC   240
ANATTCGGAC  TTCCCCGAGG  CTTACAGANT  GACNATNNCC  CTGCTTTCCA  GGCCACAGTN   300
ACCCAGGGGA  GTNTCCCNGG  CGTTNGGTNT  ACGATATCAC  TTACACTGCG  CCTGAANGCC   360
ACAGTCCTCN  GGGA                                                         374
```

( 2 ) INFORMATION FOR SEQ ID NO:48:

( i ) SEQUENCE CHARACTERISTICS:
        ( A ) LENGTH: 542 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:48:

-continued

```
AACAANTTNT TAAAACATTA CAAGGAACGT ATCCNTGAGN AGAGGGAAAA GAATTATTCC      60
ACCCTTGTGA CATGGTATTA GTCAAGTCCA TTCCCTATAA TTCCCNATCC CTAGANACAT    120
CNTGGGANGG ACCNTACCCA GTCATTTTAT NTACCCCAAC TGCGGTTAAA GTGGCTGGAG    180
TGGAGTCTTG GATACATCAC ACTTGAGTCA AATCCTGGAT ACTGCCAAAG GAACCTGAAA    240
ATCCAGGAGA CAACGCTAGC TATTCCTGTG AACCTCTAGA GGATTTGCGC CTGCTCTTCA    300
AACAACAACC AGGAGGAAAG TAACTAAAAT CATAAATCCC CATGGCCCTC CCTTATCATA    360
TTTTTCTCTT TACTGTTCTT TTACCCTCTT TCACTCTCAC TGCACCCCCT CCATGCCGCT    420
GTATGACCAG TAGCTCCCCT TACCAAGAGT TTCTATGGAG AATGCAGCGT CCCGGAAATA    480
TTGATGCCCC ATCGTATAGG AGTCTTTCTA AGGGAACCCC CACCTTCACT GCCCACACCC    540
AT                                                                  542
```

( 2 ) INFORMATION FOR SEQ ID NO:49:

( i ) SEQUENCE CHARACTERISTICS:
        ( A ) LENGTH: 67 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:49:

```
Met Ala Leu Pro Tyr His Ile Phe Leu Phe Thr Val Leu Leu Pro Ser
 1               5                  10                  15
Phe Thr Leu Thr Ala Pro Pro Pro Cys Arg Cys Met Thr Ser Ser Ser
            20                  25                  30
Pro Tyr Gln Glu Phe Leu Trp Arg Met Gln Arg Pro Gly Asn Ile Asp
            35                  40                  45
Ala Pro Ser Tyr Arg Ser Leu Ser Lys Gly Thr Pro Thr Phe Thr Ala
        50                  55                  60
His Thr His
 65
```

( 2 ) INFORMATION FOR SEQ ID NO:50:

( i ) SEQUENCE CHARACTERISTICS:
        ( A ) LENGTH: 279 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:50:

```
RCCACATCCA CCTTTAAACA CGGGGNTTGC AAANAAGATN ACACTTGACC AATCAGAGAG     60
NTCANTAAAA TGATNATTNG GCAAAAACAG GAGGTAAAGA AATAGCCAAT CATCTATTGC   120
CTGAGAGCAC AGCAGGAGGG ACAATGATCG GGATATAAAC CCAAGTTTTN GAGCCGGCAA   180
CGGCAACCCC CTTTGGGTCC CCTCCCTTTG TATGGGAGCT NTGTTTTCAT GCTATTTCAN   240
TNTATTAAAT NTTGCAACTG CAAAAAAAAA AAAAAAAA                           279
```

( 2 ) INFORMATION FOR SEQ ID NO:51:

( i ) SEQUENCE CHARACTERISTICS:
        ( A ) LENGTH: 338 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:51:

| | | | | | |
|---|---|---|---|---|---|
| AGCGGCCGCG | CCATCCCCAT | CAAGCAGGGG | ATCCTGCTAA | AGCGGAGCGG | CAAGTCCCTG | 60 |
| AACAAGGAGT | GGAAGAAGAA | GTATGTGACG | CTCTGTGACA | ACGGGCTGCT | CACCTATCAC | 120 |
| CCCAGCCTGC | ATCTTGGTGC | GCTGTCTGTG | CCCTCTGCCA | ACAGTGGAGG | CAGCGAGGAT | 180 |
| GAAGAGGAGT | GGCAAGGGGT | GTCTTGGATG | TGGAAAAAAA | TGTGGGTTGT | GGGGTTGGGC | 240 |
| TGGGTTTTGG | TTTCAGTANA | NGAAACACAG | CCAGCTGGAG | ANCANAACTC | ACGGGGGTTG | 300 |
| GTGGCTTTTC | ANAATCACCC | GGCTGGTGGC | TGANCTAA | | | 338 |

( 2 ) INFORMATION FOR SEQ ID NO:52:

( i ) SEQUENCE CHARACTERISTICS:
( A ) LENGTH: 387 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:52:

| | | | | | |
|---|---|---|---|---|---|
| AAGTAGGCAA | GGGATAATAA | CCAAAGAAGN | AAATTTCATG | AAGACTAGAC | ATCATAAAGC | 60 |
| ATAATTTTAA | TAGTCACTCA | ACCAAGTATT | TTTTATTTTT | TATGGATACT | CTGAATGGCA | 120 |
| ATTAAATGTG | AAACCCAGTT | TCTTGGGCAA | GTCAAATTST | GGNATCACAT | CCACCTAAAT | 180 |
| TAAAATGACT | AGCTCGTATT | TTCCCCATCT | TCAAGTTTCA | CATCCTGGTC | ATCAAAAGAC | 240 |
| TCGACAGCAA | GACTTAGAAT | GMAAAAGGGT | ACTTGTTTAT | ATTAATATTT | TTTACTTGAA | 300 |
| CACGTGTAGC | TTGCAGCAGG | TTCTTGATGA | ATGTGCTTTG | TGTCCAAAAT | GCCTCCCCAT | 360 |
| TGTACACAGG | TGTACACCAT | GCATGCA | | | | 387 |

( 2 ) INFORMATION FOR SEQ ID NO:53:

( i ) SEQUENCE CHARACTERISTICS:
( A ) LENGTH: 67 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:53:

```
Met Thr Ser Ser Tyr Phe Pro His Leu Gln Val Ser His Pro Gly His
 1               5                  10                  15

Gln Lys Thr Arg Gln Gln Asp Leu Glu Xaa Lys Arg Val Leu Val Tyr
            20                  25                  30

Ile Asn Ile Phe Tyr Leu Asn Thr Cys Ser Leu Gln Gln Val Leu Asp
        35                  40                  45

Glu Cys Ala Leu Cys Pro Lys Cys Leu Pro Ile Val His Arg Cys Thr
    50                  55                  60

Pro Cys Met
65
```

( 2 ) INFORMATION FOR SEQ ID NO:54:

( i ) SEQUENCE CHARACTERISTICS:
( A ) LENGTH: 348 base pairs
( B ) TYPE: nucleic acid
( C ) STRANDEDNESS: double
( D ) TOPOLOGY: linear (i i) MOLECULE TYPE: cDNA (x i) SEQUENCE DESCRIPTION: SEQ ID NO:54:

| | | | | | | |
|---|---|---|---|---|---|---|
| CAAACCCTAA | ACCCTGGCAG | GAAGCATGTC | GAGGAAGGAG | TTCCGGCAAC | TCCAGAGGNT | 60 |
| CCGACAGAAN | TNTGGGCTGA | GCCTGGNTNT | CNTNTCCAGC | AAGGGTTTCG | CCTGAGCCCC | 120 |
| AAGGGCATCG | GGANTGGNGA | CTCACCTATG | GATGGGGGCC | GGGGAGACAG | GACACACAGA | 180 |
| AGATGAGTTT | GTGGGCCAGC | CNTGAGCCCC | GCGCCNGATT | TTNGCCGGCC | CAAGAGAGCC | 240 |
| CGCCGCAGCT | TCCCCCATTT | TGCAGCCAGC | GGAGCCATTC | ACACAATCAC | CTTCTGTTAA | 300 |
| TTNTATCTGC | AACATCAATT | AAATTGTTTG | TAGAAACTAA | AAAAAAA | | 348 |

(2) INFORMATION FOR SEQ ID NO:55:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="oligonucleotide"

(x i) SEQUENCE DESCRIPTION: SEQ ID NO:55:

| | | | |
|---|---|---|---|
| TNAGATCCAA | CAGTCACGTT | CACGAAACC | 29 |

(2) INFORMATION FOR SEQ ID NO:56:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="oligonucleotide"

(x i) SEQUENCE DESCRIPTION: SEQ ID NO:56:

| | | | |
|---|---|---|---|
| GNTGAAGCAT | GCCCAATTTC | ATTTCCTCT | 29 |

(2) INFORMATION FOR SEQ ID NO:57:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="oligonucleotide"

(x i) SEQUENCE DESCRIPTION: SEQ ID NO:57:

| | | | |
|---|---|---|---|
| TNCAAGTTGA | GTTGTACAGA | AGCCCAAGA | 29 |

(2) INFORMATION FOR SEQ ID NO:58:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc ="oligonucleotide"

(x i) SEQUENCE DESCRIPTION: SEQ ID NO:58:

| | | | |
|---|---|---|---|
| ANTGTTCTCT | GGCTTGTCAG | GGAAGACTG | 29 |

( 2 ) INFORMATION FOR SEQ ID NO:59:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:59:

GNTGTGAGAA GACCACTCGG TGATGACCT      29

( 2 ) INFORMATION FOR SEQ ID NO:60:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:60:

TNGAGTCTGG GTGGTAGACA AATCATGCA      29

( 2 ) INFORMATION FOR SEQ ID NO:61:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:61:

ANGGACGGTA TATATCACCA TGAACAAGT      29

( 2 ) INFORMATION FOR SEQ ID NO:62:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:62:

ANAGGCAGGA GGAGACGGGA TTGATGGTT      29

( 2 ) INFORMATION FOR SEQ ID NO:63:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide"

( x i ) SEQUENCE DESCRIPTION: SEQ ID NO:63:

ANAAGCGTCA TGCAGAGCCA TGATGAGGG      29

( 2 ) INFORMATION FOR SEQ ID NO:64:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="oligonucleotide"

( x i ) SEQUENCE DESCRIPTION: SEQ ID NO:64:

ANAAATGTAG CAGGCTTGGC TTGCAGCAG                                29

( 2 ) INFORMATION FOR SEQ ID NO:65:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="oligonucleotide"

( x i ) SEQUENCE DESCRIPTION: SEQ ID NO:65:

ANGACCCATT TCCAGTCCAA ATCTTTGAC                                29

( 2 ) INFORMATION FOR SEQ ID NO:66:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="oligonucleotide"

( x i ) SEQUENCE DESCRIPTION: SEQ ID NO:66:

GNCAAGGTGT CTGTAGGAGA AACTATATA                                29

( 2 ) INFORMATION FOR SEQ ID NO:67:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="oligonucleotide"

( x i ) SEQUENCE DESCRIPTION: SEQ ID NO:67:

ANCCAGGGCT ATACAGAGAA ACCCTGTCT                                29

( 2 ) INFORMATION FOR SEQ ID NO:68:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="oligonucleotide"

( x i ) SEQUENCE DESCRIPTION: SEQ ID NO:68:

GNTCTTGAAG AAGTAGCCCA GGGTGAGGA                                29

(2) INFORMATION FOR SEQ ID NO:69:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="oligonucleotide"

(xi) SEQUENCE DESCRIPTION: SEQ ID NO:69:

CNGGTAAAGG TGATGTTGAC ACTGTAGGA     29

(2) INFORMATION FOR SEQ ID NO:70:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="oligonucleotide"

(xi) SEQUENCE DESCRIPTION: SEQ ID NO:70:

CNTCCTGGTT GTTGTTTGAA GAGCAGGCG     29

(2) INFORMATION FOR SEQ ID NO:71:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="oligonucleotide"

(xi) SEQUENCE DESCRIPTION: SEQ ID NO:71:

TNGCCCAAGA AACTGGGTTT CACATTTAA     29